United States Patent
Eitan et al.

(10) Patent No.: US 10,894,131 B2
(45) Date of Patent: Jan. 19, 2021

(54) METHODS CIRCUITS DEVICES ASSEMBLIES SYSTEMS AND ASSOCIATED COMPUTER EXECUTABLE CODE FOR SENSING AND ANALYZING FLUID CHARACTERISTICS WITHIN A CONDUIT OF A MEDICAL DEVICE AND AIR BUBBLES

(71) Applicant: Q-CORE MEDICAL LTD., Netanya (IL)

(72) Inventors: Boaz Eitan, Hofit (IL); Andrei Yosef, Even Yehuda (IL); David Mizrahi, Netanya (IL); Ram Shtoltz, Tel Aviv (IL); Rafi Greenfield, Alfei Menashe (IL)

(73) Assignee: Q-CORE MEDICAL LTD., Netanya (IL)

( * ) Notice: Subject to any disclaimer, the term of this patent is extended or adjusted under 35 U.S.C. 154(b) by 135 days.

(21) Appl. No.: 15/740,365

(22) PCT Filed: Jun. 29, 2016

(86) PCT No.: PCT/IB2016/053873
§ 371 (c)(1),
(2) Date: Dec. 28, 2017

(87) PCT Pub. No.: WO2017/002023
PCT Pub. Date: Jan. 5, 2017

(65) Prior Publication Data
US 2018/0200456 A1  Jul. 19, 2018

Related U.S. Application Data

(60) Provisional application No. 62/185,737, filed on Jun. 29, 2015, provisional application No. 62/278,617, filed on Jan. 14, 2016.

(51) Int. Cl.
*A61M 1/36* (2006.01)
*A61M 5/36* (2006.01)
(Continued)

(52) U.S. Cl.
CPC ........ *A61M 5/365* (2013.01); *A61M 5/16877* (2013.01); *G01N 15/10* (2013.01);
(Continued)

(58) Field of Classification Search
CPC .............. A61M 5/365; A61M 5/16877; G01N 15/1429; G01N 15/1459; G01N 2015/0011; G01N 2015/1486
(Continued)

(56) References Cited

U.S. PATENT DOCUMENTS 5,843,035 A * 12/1998 Bowman ............... A61M 5/365
604/122
8,142,400 B2 * 3/2012 Rotem .............. A61M 5/14228
604/153

(Continued)

FOREIGN PATENT DOCUMENTS

WO    2009042061 A2   4/2009
WO    2009047721 A2   4/2009

OTHER PUBLICATIONS

Extended European Search Report, EP Application No. 16817348.2, dated Jun. 21, 2019.
(Continued)

*Primary Examiner* — Ricky Ngon
(74) *Attorney, Agent, or Firm* — The Roy Gross Law Firm, LLC; Roy Gross

(57) ABSTRACT

The present invention includes methods, circuits, devices, assemblies, systems and associated computer executable code for monitoring medical conduits, sensing and measuring parameters of fluids (liquid and/or gas) within medical
(Continued)

conduits and/or processing sensed/measured parameters of fluids within medical conduits. The present invention further includes medical infusion devices and/or systems including the monitoring, sensing, measuring and analyzing devices and methods described herein.

15 Claims, 29 Drawing Sheets

(51) Int. Cl.
    *G01N 15/14*     (2006.01)
    *G01N 15/10*     (2006.01)
    *A61M 5/168*     (2006.01)
    *G01N 15/00*     (2006.01)

(52) U.S. Cl.
    CPC ..... *G01N 15/1429* (2013.01); *G01N 15/1459* (2013.01); *G01N 2015/0011* (2013.01); *G01N 2015/1062* (2013.01); *G01N 2015/1486* (2013.01)

(58) Field of Classification Search
    USPC .......................................................... 702/45
    See application file for complete search history.

(56) References Cited

U.S. PATENT DOCUMENTS

| | | | |
|---|---|---|---|
| 2003/0141468 A1* | 7/2003 | Malmstrom | A61M 5/365 250/573 |
| 2005/0107923 A1* | 5/2005 | Vanderveen | A61M 5/16854 700/282 |
| 2006/0173412 A1* | 8/2006 | Susi | F04B 43/082 604/123 |
| 2006/0189926 A1* | 8/2006 | Hall | A61B 5/14546 604/66 |
| 2007/0123781 A1* | 5/2007 | Callahan | A61B 5/036 600/483 |
| 2007/0179435 A1* | 8/2007 | Braig | A61B 5/145 604/66 |
| 2008/0283296 A1 | 11/2008 | Zamora et al. | |
| 2009/0293588 A1* | 12/2009 | Riley | A61M 5/365 73/19.03 |
| 2010/0212407 A1 | 8/2010 | Stringham et al. | |
| 2011/0190606 A1* | 8/2011 | Gable | A61B 5/0084 600/310 |
| 2012/0330574 A1* | 12/2012 | Ruiter | A61M 5/14212 702/45 |
| 2013/0226129 A1 | 8/2013 | Unverdorben | |
| 2014/0119954 A1* | 5/2014 | Schweitzer | A61M 5/142 417/63 |
| 2014/0121639 A1 | 5/2014 | Lowery et al. | |
| 2014/0228755 A1 | 8/2014 | Darrah et al. | |
| 2015/0367120 A1* | 12/2015 | Kusters | F16L 13/00 137/15.09 |

OTHER PUBLICATIONS

Office Action dated Jun. 23, 2020 received in Chinese Invention Patent Application No. 2016800500508 6 pages.

* cited by examiner

Fig. 4A

| No. | A/D difference between mediums | Air2Liquid/ Liquid2Air | Min/Max value (680 sam) | | Difference | Min/Max (degrade signal) | | Difference |
|---|---|---|---|---|---|---|---|---|
| 1 | 10 | Air2Liquid | 54 | 132 | 78 | 58 | 128 | 70 |
| 2 | 10 | Air2Liquid | 52 | 150 | 98 | 68 | 123 | 55 |
| 3 | 10 | Air2Liquid | 53 | 127 | 74 | 73 | 126 | 53 |
| 4 | 10 | Air2Liquid | 57 | 126 | 69 | 57 | 124 | 67 |
| 5 | 10 | Air2Liquid | 57 | 133 | 76 | 57 | 125 | 68 |
| 6 | 10 | Liquid2Air | 72 | 127 | 55 | 72 | 126 | 54 |
| 7 | 7 | Liquid2Air | 68 | 136 | 68 | 68 | 136 | 68 |
| 8 | 7 | Liquid2Air | 76 | 142 | 66 | 76 | 141 | 65 |
| 9 | 7 | Liquid2Air | 76 | 141 | 65 | 80 | 140 | 60 |
| 10 | 7 | Liquid2Air | 78 | 144 | 66 | 78 | 143 | 65 |
| 11 | 7 | Liquid2Air | 79 | 145 | 66 | 81 | 143 | 62 |
| 12 | 9 | Air2Liquid | 51 | 131 | 80 | 83 | 129 | 46 |
| 13 | 9 | Air2Liquid | 49 | 151 | 102 | 96 | 132 | 36 |
| 14 | 9 | Air2Liquid | 56 | 146 | 90 | 77 | 145 | 68 |
| 15 | 9 | Air2Liquid | 56 | 143 | 87 | 72 | 142 | 70 |
| 16 | 10 | Air2Liquid | 54 | 100 | 46 | 54 | 96 | 42 |
| 17 | 10 | Air2Liquid | 31 | 104 | 73 | 34 | 104 | 70 |

The signals were measured using LabView.

The sample rate is 400 samples per second.

Original sampling is 680 samples per cycle of the pump.

Degrade sampling signal is 28 samples per cycle of the pump.

METHODS CIRCUITS DEVICES ASSEMBLIES SYSTEMS AND ASSOCIATED COMPUTER EXECUTABLE CODE FOR SENSING AND ANALYZING FLUID CHARACTERISTICS WITHIN A CONDUIT OF A MEDICAL DEVICE AND AIR BUBBLES

FIELD OF THE INVENTION

The present invention generally relates to the field of medical devices. More specifically, the present invention relates to methods circuits devices assemblies systems and associated computer executable code for sensing and analyzing fluid characteristics within a conduit of a medical device and air bubbles therein.

BACKGROUND

Many therapeutic and diagnostic processes are performed nowadays by medical devices and/or with the assistance of medical devices. Medical devices are prevalent both in medical centers and hospitals as well as in patient's homes and on their person. Some medical devices operate by manual activation and control, whereas others include automated processors designed to operate the medical device automatically or semi-automatically.

In many cases, there is a need to transport fluid to and/or from a patient. There are many medical devices designed to transport fluid to and/or from a patient, at different levels of automation. Some are entirely manual, entirely operated and controlled by the caretaker and/or patient. Others include automated functions and/or safety features. Some rely on gravity to transport the fluid, while others include pumping mechanisms designed to push/pull the fluid to or from the patient, such as peristaltic pumps. Such pumps may include camshafts and/or one or more fingers or actuators as part of a pumping mechanism. A pump may also have a pump cycle during which a predetermined amount of fluid is caused to flow through the conduit. In some cases, the system may be designed to accurately deliver the fluid at a specific rate.

Some of the automated fluid delivery devices include components designed to detect an occlusion in the line and/or may detect and/or monitor an amount of air or gas in the line, which may be inadvertently delivered to a patient while transporting the desired fluid. Such devices may trigger an alarm and/or stop treatment if a predetermined amount of air or gas is exceeded.

SUMMARY

Modern medicine uses many automated fluid delivery systems and devices to administer anything from saline to chemotherapy to oxygen. As these systems and devices become more and more automated, such does the need to automatically sense and analyze fluid, or lack thereof, within the conduits of the systems/devices. In some systems there is a need to determine whether or not the conduits have been filled with a fluid or not (i.e. determine if the system has been primed). In some systems, it may be desirable to identify the fluid or one or more characteristics of the fluid. In some systems, the type of fluid may be important or its temperature/pressure. In some systems a combination of the above may be desired.

In addition, due to the danger involved in accidental delivery of air bubbles to a patient, it is desired in such systems and devices to detect and monitor air bubbles within the conduits to assess the related danger and automatically take preventive/remedial action when necessary.

There are many known systems for air bubble detection and conduit monitoring, however, these systems are often binary in nature, inaccurate and/or lack the means to differentiate between different fluids, thereby lacking the ability to provide much of the desired information or provide information insufficiently reliable. There is therefore a need for improvements in the sensing devices used for monitoring medical conduits, as well as the development of new devices and systems. There is further a need to improve the associated sensor signal processing and analysis to provide more of the desired information more accurately.

The present invention includes methods, circuits, devices, assemblies, systems and associated computer executable code for monitoring medical conduits, sensing and measuring parameters of fluids (liquid and/or gas) within medical conduits and/or analyzing the results. The present invention further includes medical fluid delivery devices and/or systems including the monitoring, sensing, measuring and analyzing devices and methods described herein. According to some embodiments of the present invention, there may be provided one or more of the following conduit/conduit-fluid sensing devices and/or sub-systems, either integrally, or in addition, to a medical fluid delivery system/device (for example, an IV drug/fluid delivery system, an epidural drug/fluid delivery system, a dialysis device, a syringe pump, a heart and lung machine and so on):

a. an energy sensor (such as a light sensor), possibly in combination with an associated energy emitter. According to some embodiments, an energy/light sensor may be placed to sense energy/light travelling through the conduit, possibly emitted by an associated emitter (for example, an IR emitter, a LED, an RGB emitter, an ultrasonic emitter and so on). The energy/light sensed may be analyzed to determine parameters of fluid in the conduit. Parameters of energy/light passing through the conduit may be used to determine whether the fluid is gas or liquid, identify air bubbles within a liquid and/or identify the fluid (for example, based on a spectral analysis of light travelling through it). According to further embodiments, changes in parameters of light passing through the conduit may be used to determine transitions between fluids (such as a transition from liquid to air) and/or to determine whether a given sensed air bubble is static or dynamic, and/or b. a pressure/force sensor, possibly in combination with a clamp. According to some embodiments there may be provided a sensor adapted to sense pressure/force within the conduit. According to further embodiments, the pressure/force sensor may function in combination with a clamp adapted to partially or completely obstruct flow of fluid through the conduit and/or apply pressure/force to the conduit. According to some embodiments, by measuring the change of pressure and/or rate of change of pressure within the conduit upon applying/releasing the clamp, the nature of the fluid within the conduit and/or the amounts of liquid/gas/air within the conduit may be determined. This may be done due to the fact that the changes in pressure resulting from applying and/or releasing the clamp depend on the physical characteristics of the fluid within the conduit and its pressure.

According to some embodiments of the present invention, there may be provided a processor/processing-circuitry adapted to analyze output from one or more sensors functionally associated with a medical fluid delivery system/device, to determine one or more of:

a. whether the conduit is filled with gas/air or liquid—as described herein, the determination whether the conduit is filled with gas/air or liquid may be derived from measurements of pressure within the conduit and/or changes in pressure in response to the application and/or release of pressure/clamping to the conduit. It should be noted within the context of the present application that the terms "filled with air" and/or "filled with liquid" refer to a condition where minute amounts of other substances may still be present within the respective fluid (the exact percentages being situational dependent), such that these terms should be understood to include such conditions which could also be described as "substantially filled with . . . " considering the application in question. The nature of the fluid within the conduit may also be determined from output of a light sensor associated with the conduit, i.e. based on parameters of light having passed through the fluid. According to further embodiments, both sensing techniques may be used alternatively and/or in combination as well as in combination with the techniques discussed below in sections (b)-(d). For example, the nature of the fluid may regularly be determined based on light sensing and in the event the light sensing is inconclusive, and/or at critical moments, pressure/clamping may be applied and the associated force/pressure measurements made to provide a second indication or verification. In another example, priming of a system/conduit may be verified by a pressure sensor clamp combination and a second sensor used subsequently to monitor the line, possibly using the original reading of the pressure sensor to determine starting conditions;

b. an identity and/or classification of the fluid in the conduit and/or characteristics thereof—as described herein, spectral analysis of light having passed through the conduit may be used to determine the identity of the fluid within the conduit and/or to determine one or more characteristics of the fluid;

c. identify air bubbles and their size and quantity—as described herein, analysis of light having passed through the conduit may be used to identify air bubbles within a liquid flowing through the conduit and determine their size. According to some embodiments, air bubbles may be detected and identified by detecting changes in the parameters of light having passed through the fluid which are indicative of transition between substances (boundary conditions); and d. whether a given air bubble is static or dynamic and/or a mobility of a given air bubble—as described herein, by measuring one or more of the above parameters over time and determining the rate of change of the relevant parameter, the movement, or lack thereof, of the given air bubble may be determined. Further, once a static air bubble is detected it may be monitored to detect if it becomes dynamic.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIGS. 3C-3D are flowcharts presenting exemplary algorithms for monitoring of medical conduits based on detection and analysis of sensor output indicative of transition between fluid types within the conduit, wherein FIG. 3C presents a first example of an algorithm and FIG. 3D presents a second example of a algorithm, all in accordance with some embodiments of the present invention;

FIGS. 4A-4C present results of exemplary lab experiments designed to identify signals/parameters indicative of boundary conditions within a conduit under observation in different conditions, wherein FIG. 4A presents data in table form, and FIGS. 4B and 4C present graphs, all in accordance with some embodiments of the present invention;

FIGS. 5A-5C present exemplary light sensor outputs when detecting a RGB light source through air, water, TPN 2% (representing an opaque liquid) and a mixture of ink and water designed to mimic an Iron Sucrose treatment fluid (representing a semitransparent liquid), wherein FIG. 5A presents the exemplary results in the Blue waveband, FIG. 5B presents the exemplary results in the Green waveband and FIG. 5C presents the exemplary results in the Red waveband all in accordance with some embodiments of the present invention. As can be seen, each substance absorbs a different amount of light of each wavelength, thereby creating a distinguishable spectral signature;

FIGS. 11A and 11B (depicting exemplary dynamic air bubbles) present data per sample, wherein the whole graph shows signals collected over 100 samples. FIGS. 11C and 11D (depicting exemplary static air bubbles) present data per 5 samples, wherein the whole graph shows signals collected over 1000 samples;

FIGS. 12A-12B are block diagrams of an exemplary energy based line sensing assembly, wherein FIG. 12A presents an exemplary energy based line sensing assembly designed to work in conjunction with a medical device and FIG. 12B presents an exemplary medical device including an energy based line sensing assembly, all in accordance with some embodiments of the present invention;

FIGS. 13A-13B are block diagrams of an exemplary pressure sensor based line sensing assembly, wherein FIG. 12A presents an exemplary pressure sensor based line sensing assembly designed to work in conjunction with a medical device and FIG. 12B presents an exemplary medical device including a pressure sensor based line sensing assembly, all in accordance with some embodiments of the present invention;

FIGS. 14A-14B are block diagrams of an exemplary system including an energy based line sensing assembly and a pressure sensor based line sensing assembly, wherein FIG. 14A presents a system including an energy based line sensing assembly and a pressure sensor based line sensing assembly designed to work in conjunction with a medical device and FIG. 14B presents an exemplary medical device including an energy based line sensing assembly and a pressure sensor based line sensing assembly, all in accordance with some embodiments of the present invention;

FIGS. 15A-15B are block diagrams of an exemplary system including an energy based line sensing assembly, a pressure sensor based line sensing assembly and further line sensing assemblies, wherein FIG. 15A presents a system including an energy based line sensing assembly, a pressure sensor based line sensing assembly and further line sensing assemblies designed to work in conjunction with a medical device and FIG. 15B presents an exemplary medical device including an energy based line sensing assembly, a pressure sensor based line sensing assembly and further line sensing assemblies, all in accordance with some embodiments of the present invention;

Figure 1:
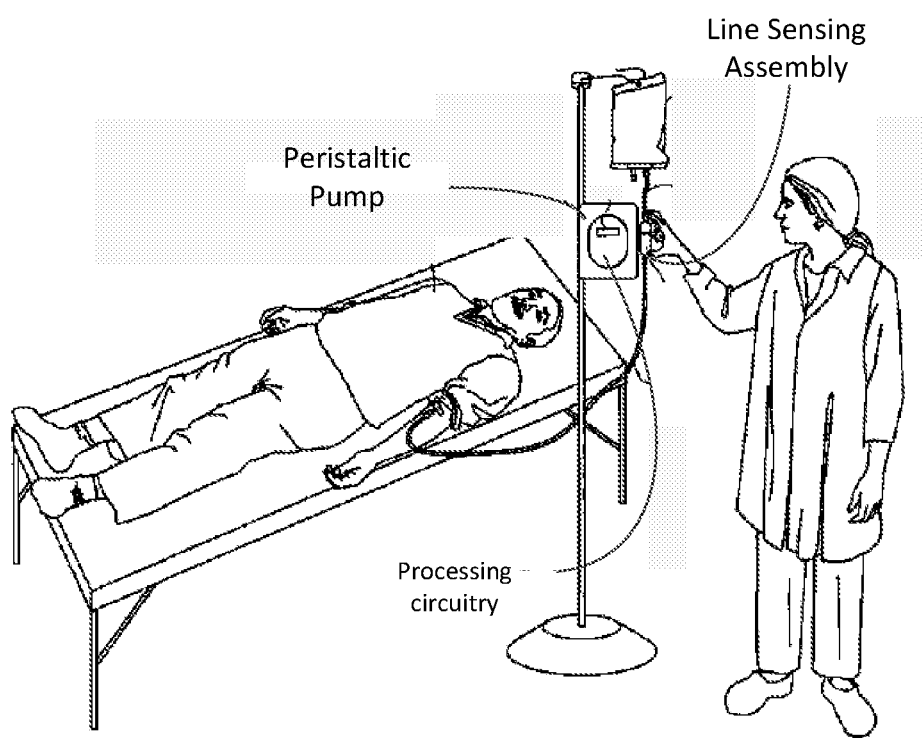
FIG. 1 is a schematic illustration of an exemplary medical infusion system connected to a patient, including a medical delivery system, line sensing assemblies and associated processing circuitry, all in accordance with some embodiments of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

It should be understood that the accompanying drawings are presented solely to elucidate the following detailed description, are therefore, exemplary in nature and do not include all the possible permutations of the present invention.

DETAILED DESCRIPTION

The following description is presented to enable any person skilled in the art to make and use the invention, and is provided in the context of particular applications of the invention and their requirements. Various modifications to the disclosed embodiments will be readily apparent to those skilled in the art and the general principles defined herein may be applied to other embodiments and applications without departing from the scope of the present invention. Thus, the present invention is not intended to be limited to the embodiments shown, but is to be accorded the widest scope consistent with the principles and features disclosed herein.

In the following detailed description, numerous specific details are set forth in order to provide a thorough understanding of the invention. However, it will be understood by those skilled in the art that the present invention may be practiced without these specific details. In other instances, well-known methods, procedures, components and circuits have not been described in detail so as not to obscure the present invention.

Unless specifically stated otherwise, as apparent from the following discussions, it is appreciated that throughout the specification discussions utilizing terms such as "processing", "computing", "calculating", "determining", or the like, refer to the action and/or processes of a processor, processing circuitry, micro-controller, computer or computing system, or similar electronic computing device, including mobile phone or any mobile device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. This apparatus may be specially constructed for the desired purposes, or it may comprise a general purpose computer, processor or micro-controller selectively activated or reconfigured by a computer program stored in the computer or phone or any other computing device. Such a computer program may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays presented herein are not inherently related to any particular computer or other apparatus. Various general purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the inventions as described herein.

It should be understood that any topology, technology and/or standard for computer networking (for example, mesh networks, infiniband connections, RDMA and so on), known today or to be devised in the future, may be applicable to the present invention.

In the following detailed description references to the figures appear in brackets. Numbers or letters appearing in brackets, such as [500], excluding paragraph numbers, should be understood to refer to elements marked within the figures by the same number and/or letter which appears in the brackets.

The present invention includes methods, circuits, devices, assemblies, systems and associated computer executable code for monitoring medical conduits, sensing and measuring parameters of fluids (liquid and/or gas) within medical conduits and/or processing sensed/measured parameters of fluids within medical conduits. The present invention further includes medical fluid delivery devices and/or systems including the monitoring, sensing, measuring and analyzing devices and methods described herein.

The present disclosure is presented in relation to medical fluid delivery systems, however, the conduit sensing assemblies described herein, as well as the associated controllers and methodologies, may be implemented in relation to other automated fluid delivery systems/pumps. Accordingly, the teachings of the present disclosure, although referring specifically to medical fluid delivery systems, should be understood to also apply to other fluid delivery systems/pumps.

According to some embodiments of the present invention, there may be provided one or more conduit/conduit-fluid sensing devices/sub-systems, either integrally, or in addition, to a medical fluid delivery system/device, as shown in FIG. 1 and FIGS. 12A-15B. The medical fluid delivery system/device may be a peristaltic pump, an infusion pump, a syringe pump, an enteral pump, a dialysis machine, a heart and lung machine or a combination of the above or any medical device configured to cause fluid to flow from a fluid source to a destination (such as a patient) at a location downstream from the medical device. The medical fluid delivery system/device may be configured to supply the fluid to a patient via: Intra-venous (IV), subcutaneous, epidural, enteral intrathecal, subarachnoid, peri-neural, neuro-axial or any other delivery method. The fluid may be any medical fluid delivered by such systems, such as saline, water, iron sucrose, Total Parenteral Nutrition (TPN), lipids, IV medication, epidural medication, blood and blood products and combinations of any of these. The conduit may be a tube, a cassette and/or may include a housing to connect the conduit to the medical device and/or interface between the conduit and the device (for example, the conduit may include a housing for mounting it on a peristaltic pump such that the pump pushes the fluid through the conduit).

According to some embodiments, AIL may be air in the line/and or conduit and/or tube. A cycle may be a pump cycle for example when the pump circuits/mechanics conclude a full round of operation. There may be several sensor samples per each pump cycle for example 1-100. LS is a light sensor. TPN (Total Parenteral Nutrition) may be an example of an opaque liquid. Fluid within this description should be understood to refer to any substance characterized by an ability to flow through a conduit, such that fluid may include gas or liquid, and even certain solids (such as gel type substances), or any combination thereof.

According to some embodiments of the present invention, there may be provided a light based line sensor (or other energy sensor, such as an ultrasonic sensor), possibly in combination with an associated light (energy) emitter, as shown in FIGS. 2, 12A-12B and 14A-15B. According to some embodiments, a light/energy sensor may be positioned to sense light/energy travelling through the conduit, possibly emitted by an associated emitter (for example, an IR emitter, a LED, an RGB emitter, an ultrasonic emitter and so on). The output of the light/energy sensor may be analyzed to determine parameters of fluid in the conduit. Parameters of light/energy passing through the conduit may be used to determine whether the fluid is gas or liquid, identify air bubbles within a liquid and/or identify the fluid (for example, based on a spectral analysis of light/energy travelling through it). According to further embodiments, changes in parameters of light/energy passing through the conduit may be used to determine transitions between fluids (such as a transition from liquid to air or liquid to air) and/or to determine whether a given sensed air bubble is static or dynamic.

According to some embodiments, a line inspection assembly may include at least one emitter functionally coupled to an emitter-line interface, wherein the emitter-line interface may facilitate transmission of energy/light/radiation released by the emitter into the line to be inspected. For example, the interface may position the emitter to emit energy/light/radiation into the conduit, possibly at a specific orientation, as shown in FIGS. 2, 12A-12B and 14A-15B. The interface may position the emitter in relation to the conduit and an associated light sensor so as to emit energy/light/radiation through the conduit to the sensor. The line inspection assembly may also include at least one sensor functionally coupled to a sensor-line interface, wherein the sensor-line interface may facilitate reception/detection/sensing of energy released into the line by the at least one emitter. For example, the interface may position the sensor to receive/detect/sense energy/light/radiation arriving from the conduit, possibly at a specific orientation. The interface may position the sensor in relation to the conduit and an associated emitter so as to sense/detect/receive energy/light/radiation emitted by the emitter through the conduit. According to further embodiments, other forms of energy emitters and respective sensors may be similarly implemented (for example, an ultrasonic emitter+sensor). According to yet further embodiments, an emitter may be positioned next to an associated sensor, to perform Doppler test type measurements.

Figure 12A:
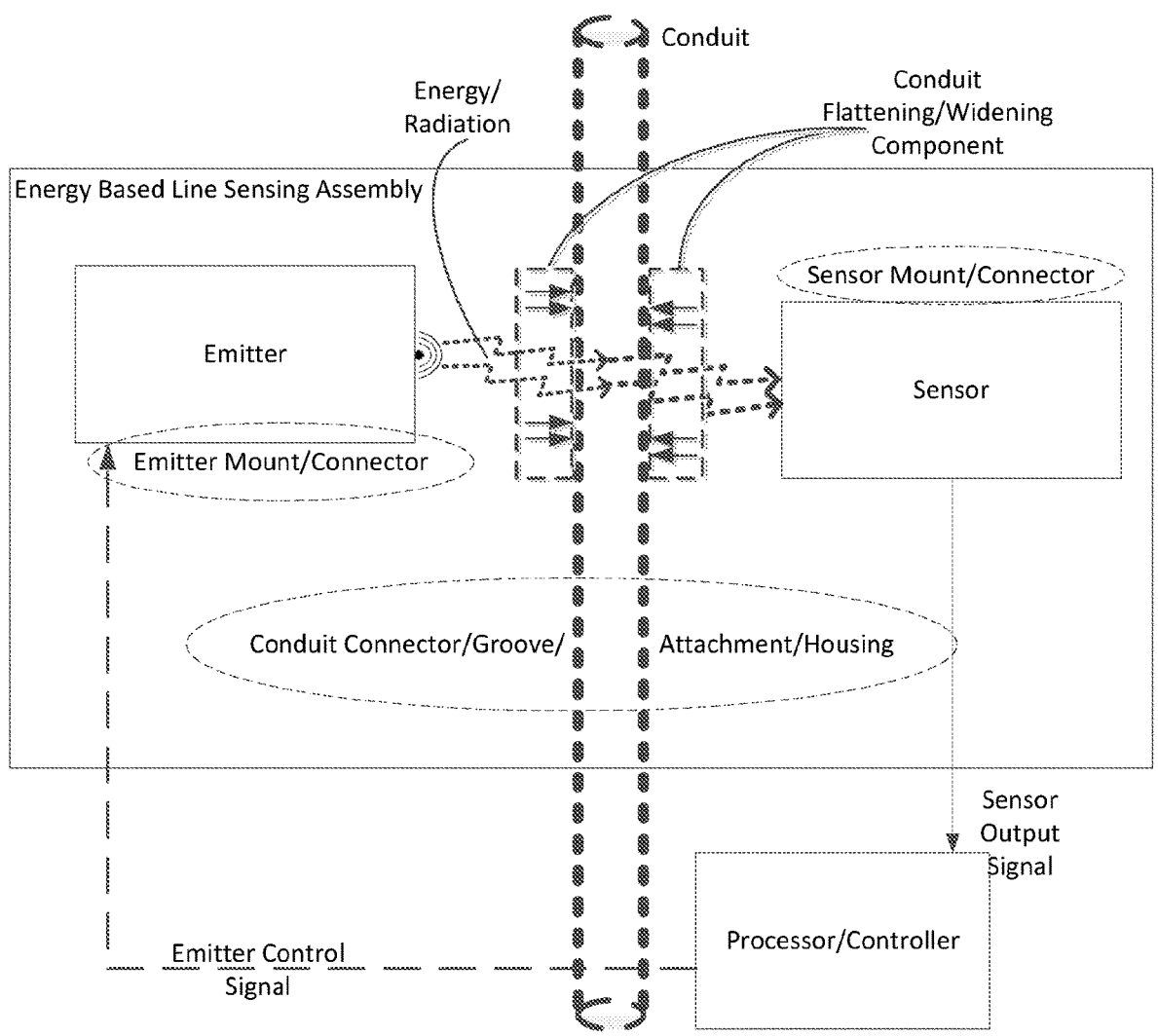
Figure 12B:
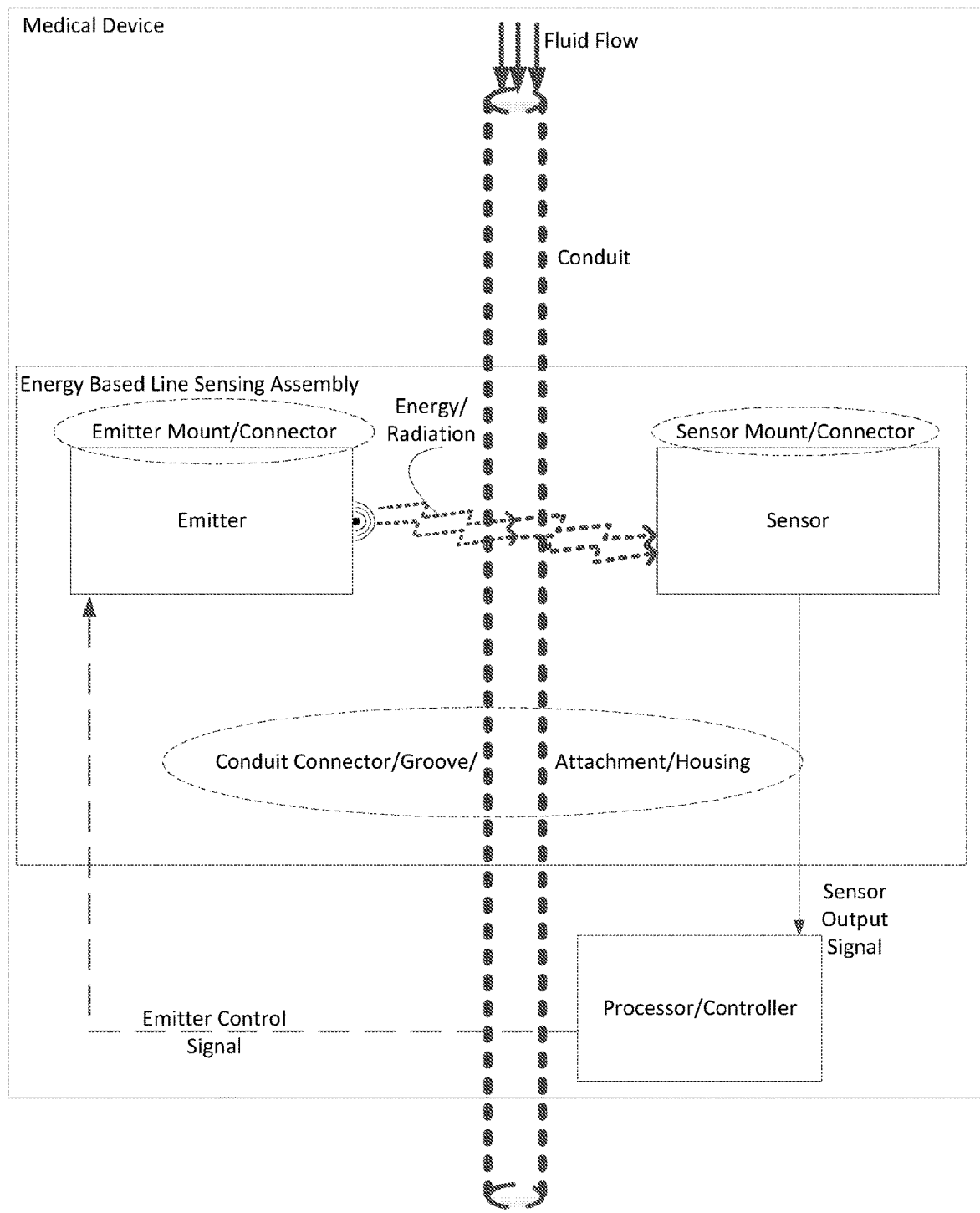
Figure 13A:
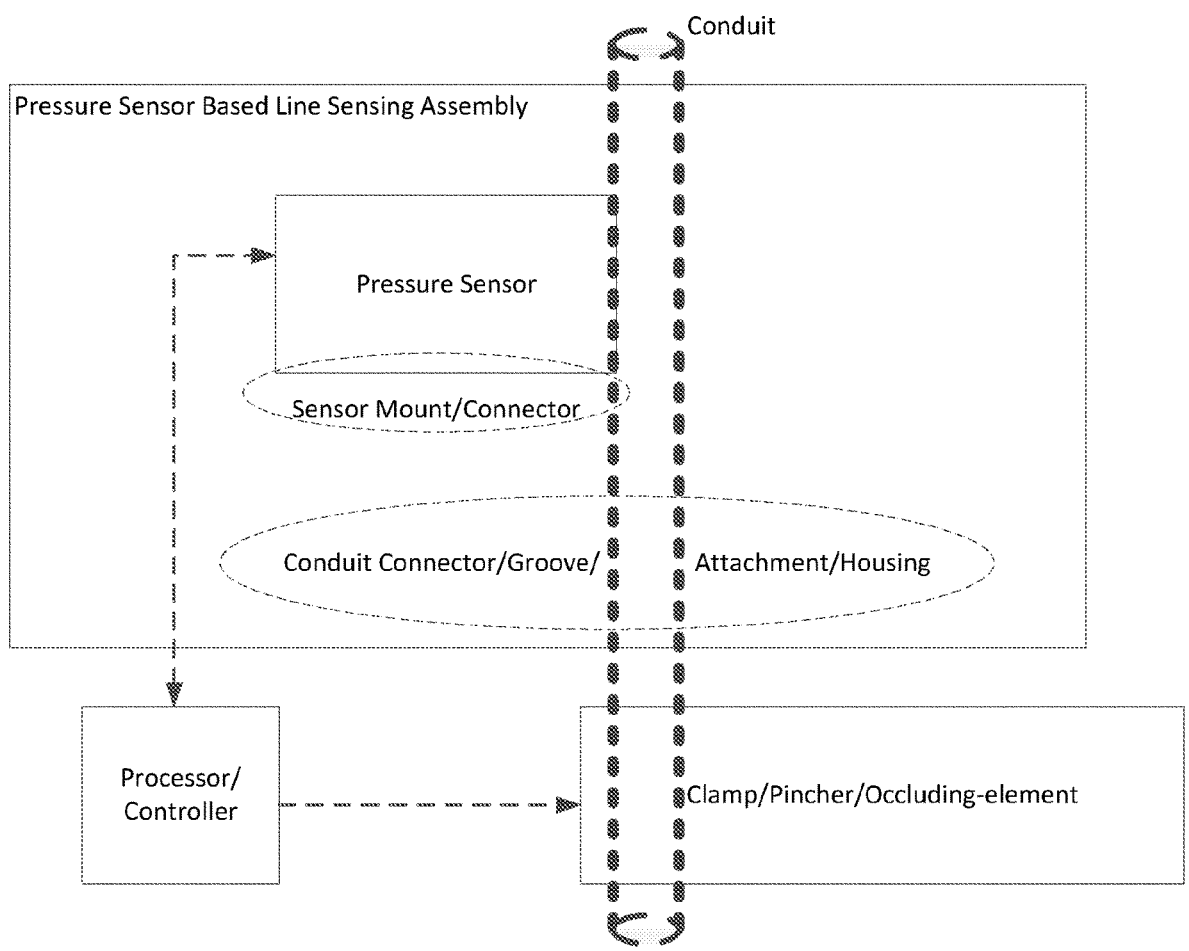
Figure 13B:
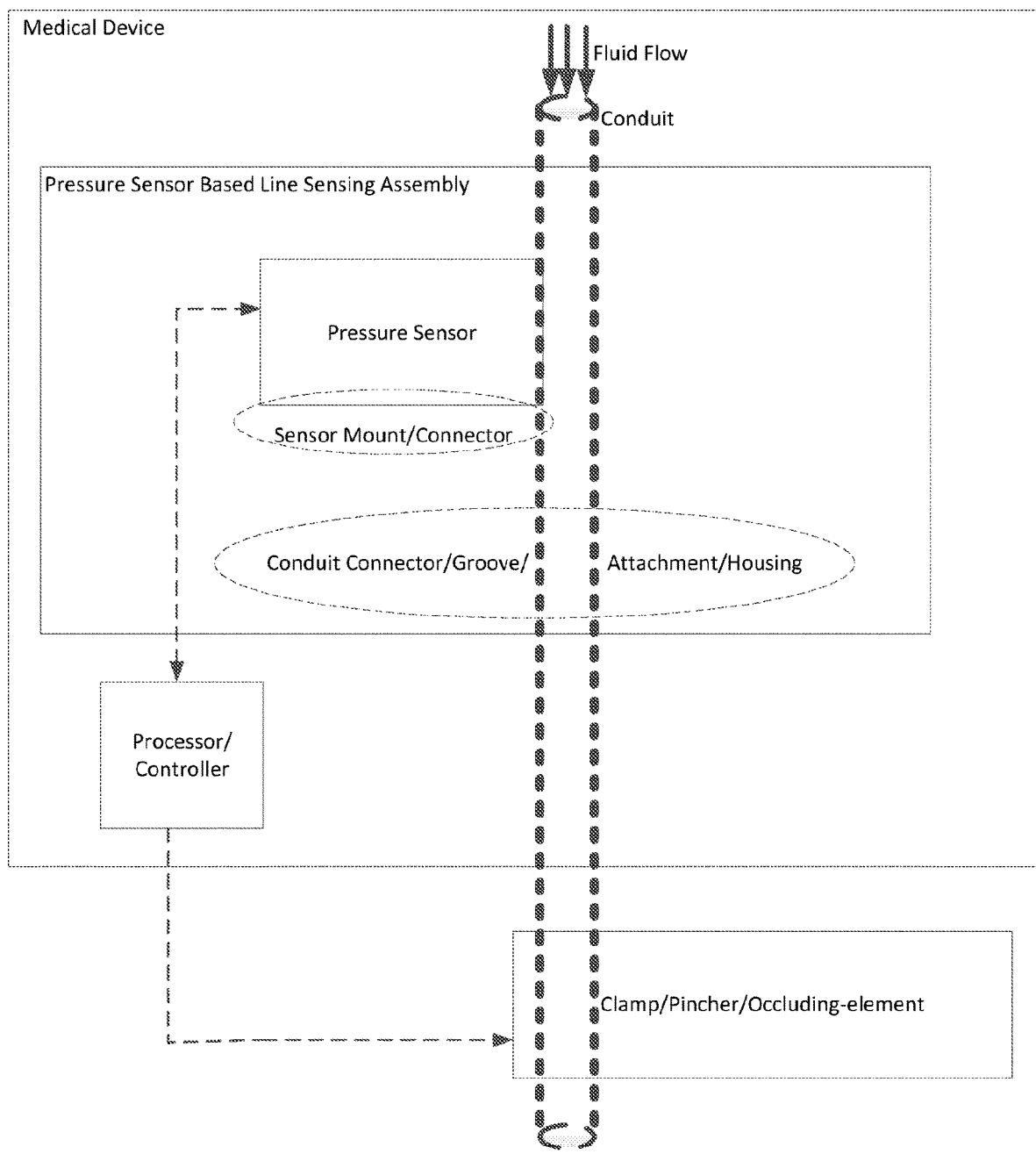

According to some embodiments, a line inspection assembly may further include physical adaptations designed to depress/squeeze or otherwise flatten the conduit/tube in the area sensed by the light sensor to improve the operation of the light sensor, as illustrated in FIG. 12A. According to some embodiments, a pressure sensing element as described herein may also serve to "flatten" the conduit/tube to a degree to improve the functionality of the light sensing components. Of course, in such assemblies, the light sensor must be positioned within, or adjacent to, the pressure sensing area.

Figure 2:
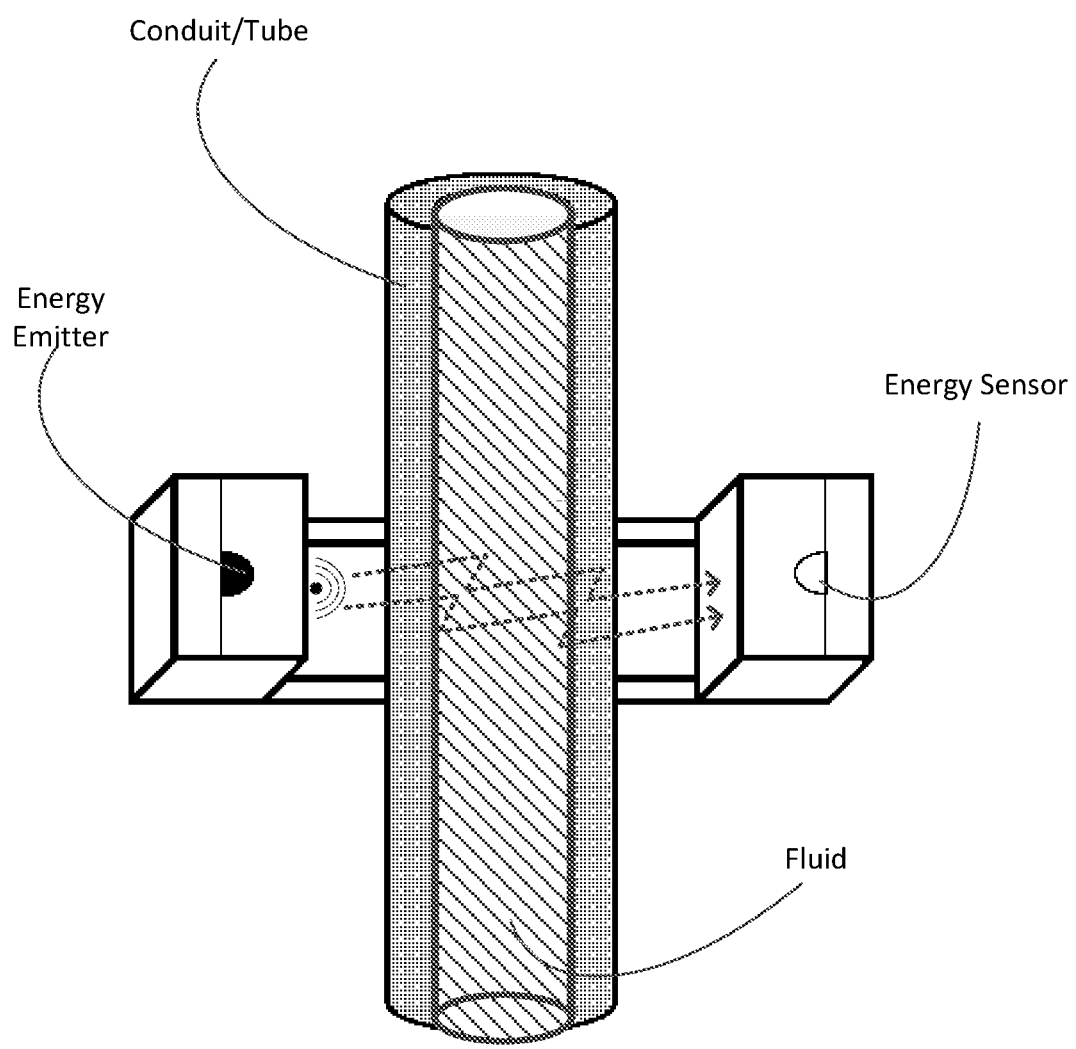
FIG. 2 is an illustration of an exemplary energy based medical line sensing assembly, in accordance with some embodiments of the present invention.

According to some embodiments, interfaces as described above (emitter-line interface and/or sensor-line interface) may be implemented by one interface or separate interfaces. These interfaces may include physical components for facilitating the operation of the emitter/sensor and its positioning in relation to the conduit. These components for mounting/positioning the sensor assemblies described herein and/or connecting them to an associated medical device and/or conduit, may also be referred to as connectors, mounts, attachments, grooves and/or housings. For example, an interface may be provided as shown in FIG. 2, including physical mounts for the emitter and sensor, positioning them on either side of the conduit so as to facilitate measurement of light emitted from the emitter, by the sensor. The interface may further include wiring and/or other electrical adaptations for facilitating function of the emitter/sensor and/or physical adaptations/connectors for mounting/connecting the sensor/emitter assembly/interface to a medical device/conduit. The interface may be integral to the medical device or a separate component adapted to attach/mount on the device or conduit. In further embodiments, sensing assemblies as described herein may be implemented as separate devices/components designed to connect directly to a conduit. According to some embodiments, as shown in FIGS. 12A-15B, the sensing assemblies described herein, and/or their respective interfaces, may include physical adaptations designed to position and/or secure a conduit they are operating upon in the correct position for their operation by means of a connector, groove/channel, attachment, housing and/or any other component designed to collocate the assembly and conduit.

According to some embodiments, a signal processing circuit and/or an associated processor may receive and analyze an electrical signal generated by the assembly sensor. The signal processing circuit/processor may generate an output characterizing a substance within the conduit and currently/recently sensed/detected by the sensor. The output may be in the form of raw data and/or fully/partially processed data. The signal processing circuit may further include a list of: (1) sensor output thresholds, (2) sets of sensor output values/thresholds, (3) gradient thresholds (sensor output change rate thresholds) or (4) other defined sensor output patterns, at which to activate and/or otherwise collect information from one or more other sensors functionally associated with the line. For example, sensor readings typical of an air bubble may trigger activation of a second sensor/sensor-assembly designed to verify whether an air/gas bubble is within the line and/or to determine/verify the size of the air/gas bubble.

According to some embodiments, an energy based line inspection assembly emitter may be a photonic/light emitting diode (LED), for example an infrared LED. According to further embodiments, the emitter may be a multispectral photonic/light emitter, for example a Red-Green-Blue (RGB) LED which can produce photons of wavelengths within three separate wavelength ranges or bands. According to each of these two embodiments, the line inspection assembly may include one or more photonic/light sensors whose spectral sensing characteristics substantially correspond to sense photons of the emitter(s) used in the same assembly.

According to some embodiments, a line inspection assembly including an emitter and a correlating sensor may be utilized to detect fluid transitions within the conduit (for example, transition from air-liquid, liquid-air, Iron Sucrose to water and so on). Accordingly, a signal processing circuit may receive and analyze an electrical signal generated by the assembly sensor to detect parameters indicative of fluid transitions within the conduit (boundary conditions), illustrated in FIG. 3A. According to some embodiments, upon detection of boundary conditions signal information may be analyzed to detect/analyze/determine the nature of the transition (for example, from liquid to air/gas, from air/gas to liquid, from opaque liquid to semitransparent liquid and so on).

Figure 3A:
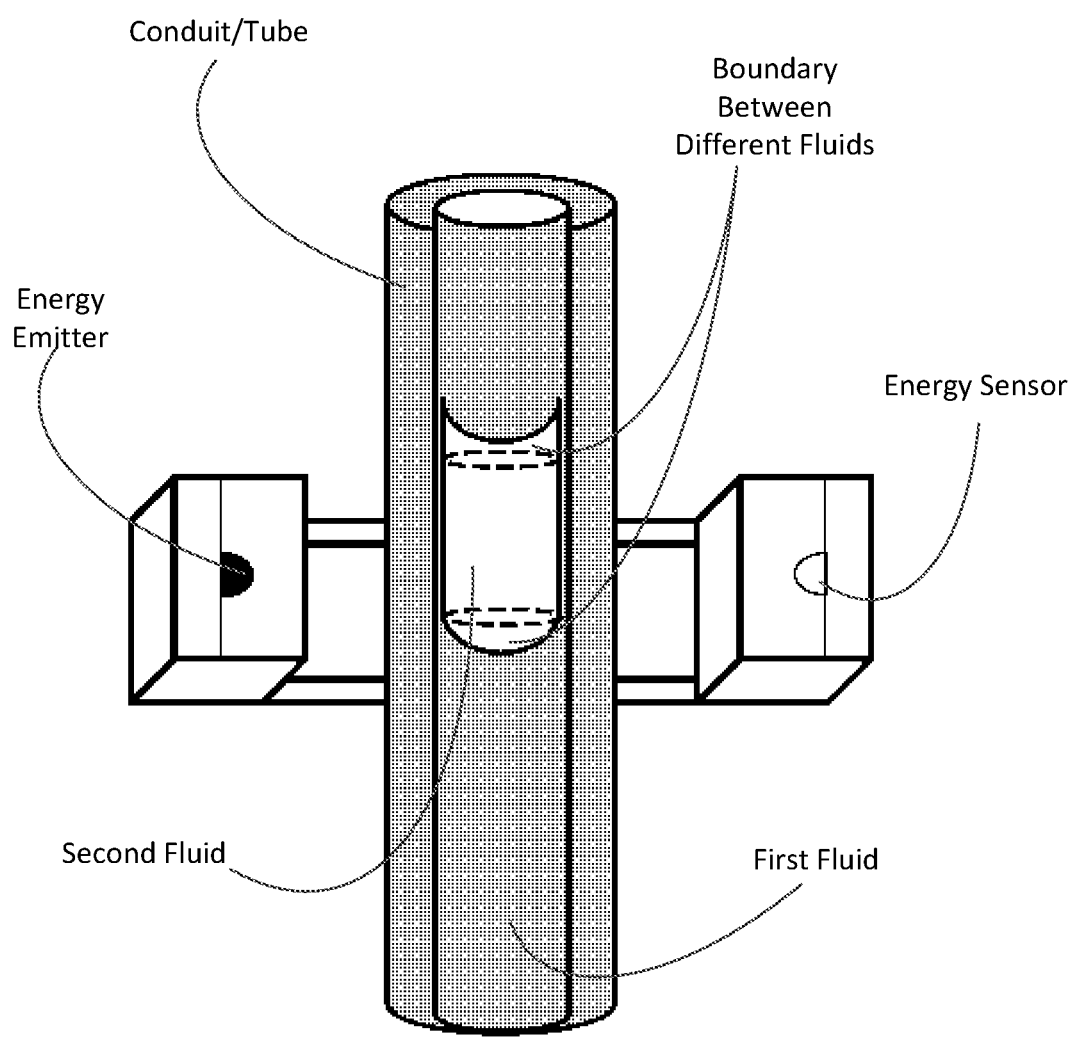
FIG. 3A is an illustration of an exemplary energy based medical line sensing assembly, illustrating the transitions between fluids within the line, all in accordance with some embodiments of the present invention.
Figure 3B:
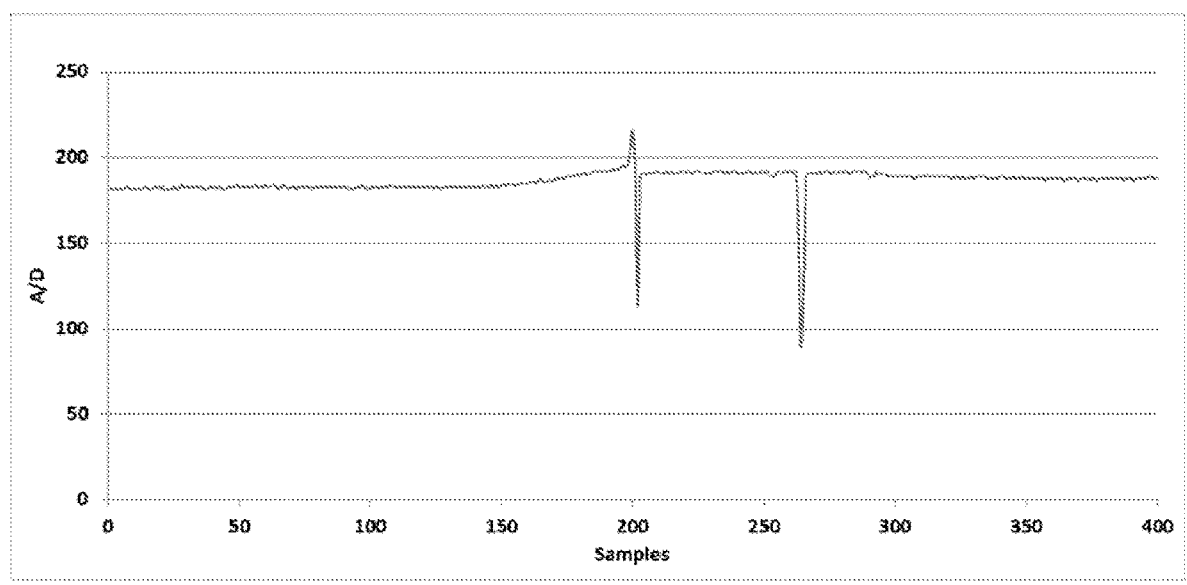
FIG. 3B is a graph of exemplary light sensor output during the passing of an air bubble through a monitored medical conduit, showing exemplary sensor output indicative of transition between liquid to gas or vice-versa, all in accordance with some embodiments of the present invention.

FIG. 3A presents an exemplary light based line inspection assembly for detecting boundary conditions. FIG. 3B shows exemplary light sensor output during the passing of an air bubble through an exemplary medical conduit monitored by the light sensor. As is evident from FIG. 3B, the value of the electrical signal provided by the assembly sensor may be substantially similar or relatively close for both liquid and gas, however, in the transition between liquid and air (in this example) a boundary/edge condition may be detected (for example, a spike in the output). Signal analysis may be used by the signal processing circuit to decipher if the transition was from liquid to gas/air or vice versa. Transition from air to liquid may (a) translate to a different output from the sensor (i.e. a different effect on the light) than transition from liquid to air, or (b) an initial condition may be utilized to decipher if the transition is from gas to liquid or vice versa and/or a combination of (a) and (b) may be utilized. These distinctive patterns can be identified by the signal processing circuitry to determine the nature of each detected transition (boundary condition), so that an associated medical device can allow the liquid to be administered while detection of air or gas may cause the medical device to emit an alert and/or stop therapeutic functionality of the medical device. In other words, sensor signal output fluctuations may be monitored and compared to fluctuation patterns typical of transition between fluids/mediums. In this manner transitions between fluids/mediums can be identified and monitored. Typical fluctuation patterns can be defined based on experimentation and may further be condition dependent—i.e. defined differently based on the system/device parameters and/or environmental parameters.

An Exemplary Boundary Condition Detection/Spike Detection methodology might be:
Exemplary Sampling Rate:
  60 Samples per cycle
Parameters:
  Maximal and Minimal values per Cycle
  Cycle Average
Spike detecting trigger:
  If (Max Min)>20 [A/D] in one cycle=Spike
An exemplary Boundary Condition Detection Algorithm might be:
Parameters:

--- n - Cycle Number
TruLiquid - Moving average of liquid cycles =
initialization: TruLiquid [1] = Current_AS
TruLiquid [n] = (TruLiquid [n − 1] * 7 + Current_AS)/8
TruAir - Moving average of air cycles =
initialization: TruAir [1] = Current_AS
TruAir [n] = (TruAir [n − 1] * 7 + Current_AS)/8
AS - Bubble Detector Signal averaged over 1 cycle
Current_AS = (Σ Sample)/Number_of_Samples
Air_Liquid_Delta - The minimum significant delta between liquid and air = 10
Spike Counter - Counts the number of spikes detected

```
Spike_Threshold = 20
CM—Calibration Margin = 22
EAM—EEPROM Air Margin = 15
Sampling Rate - The sampling rate per cycle = 60
AM—Added Margin - Extra margin added to EAM for hysteresis
   purposes = 10
```

Figure 3C:
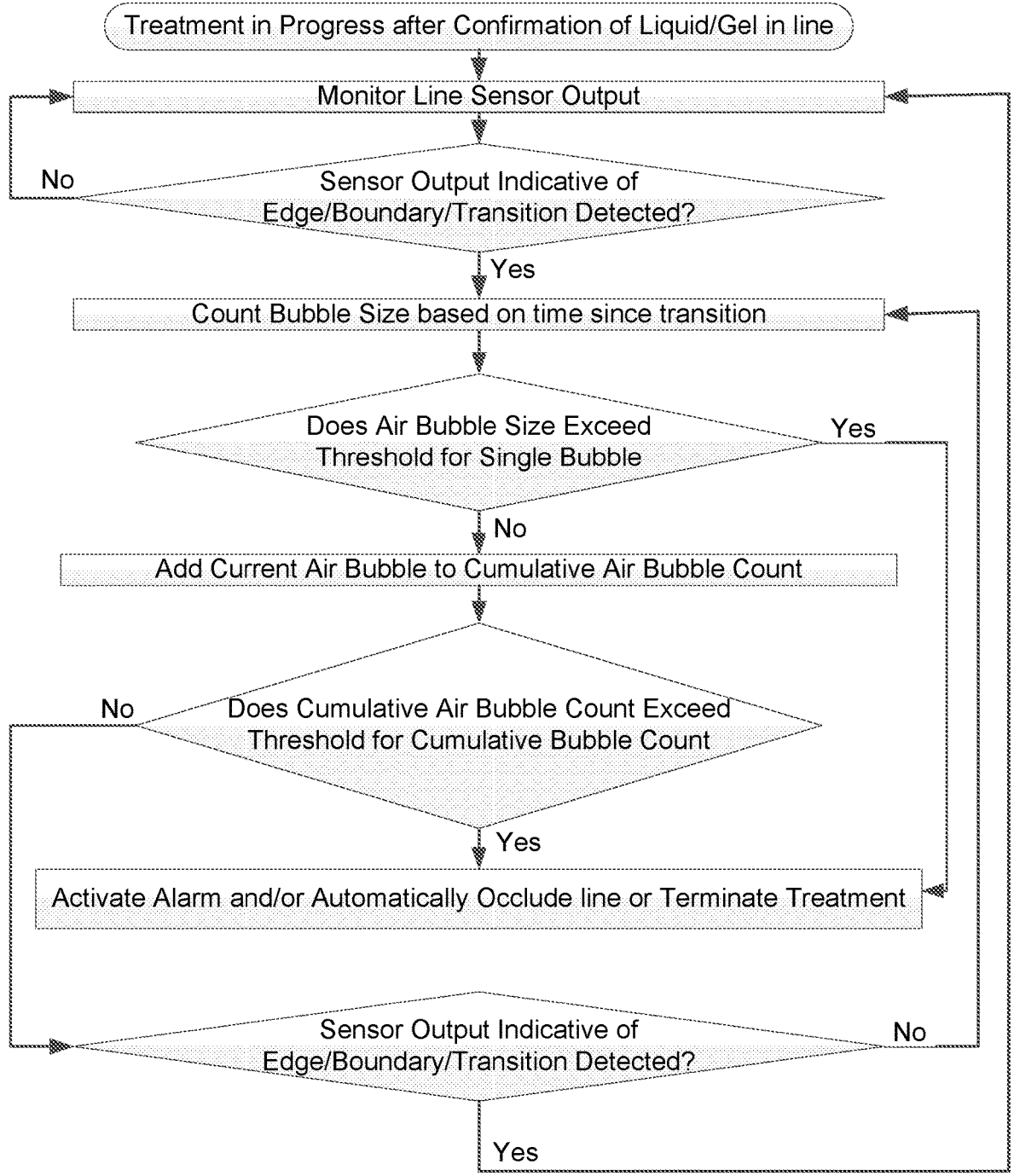
Figure 3D:
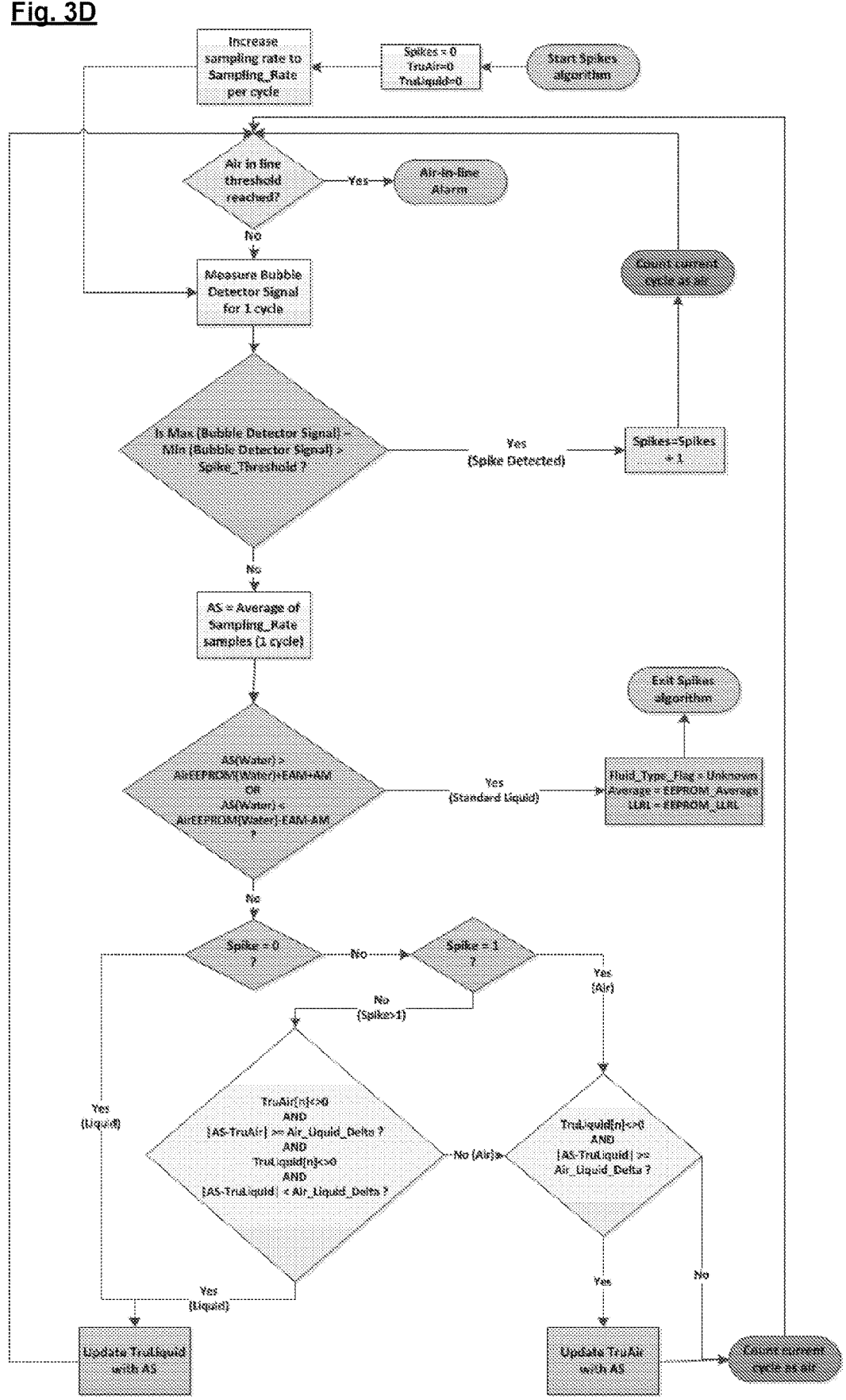

FIG. 3C illustrates an exemplary algorithm for identifying and counting air bubbles in a medical conduit using output of a light sensor associated with a line inspection assembly. FIG. 3D presents another specific algorithm of the same, with reference to the following parameters:

```
n - Cycle Number
AS (Averaged Signal) - Bubble Detector Signal averaged over 1 cycle
Current_AS = (Σ Samples_per_cycle)/Number_of_Samples
TruLiquid - Moving average of liquid cycles =
initialization: TruLiquid [1] = Current_AS
TruLiquid [n] = (TruLiquid [n – 1] * 7 + Current_AS)/8
TruAir - Moving average of air cycles =
initialization: TruAir [1] = Current_AS
TruAir [n] = (TruAir [n – 1] * 7 + Current_AS)/8
Air_Liquid_Delta - The minimum significant delta between liquid and
   air = 10
Spikes - Counts the number of spikes detected
Spike_Threshold = 20
CM—Calibration Margin = 22
EAM—EEPROM Air Margin = 25
Sampling_Rate - The sampling rate per cycle = 60 samples
AM—Added Margin - Extra margin added to EAM for hysteresis
   purposes = 10
```

As can be seen in the above example algorithm and in FIGS. 3C-3D, by detecting parameters indicative of transition between liquid to air (written liquid2air in the table) or air to liquid (air2liquid), air bubbles can be detected, measured/estimated and counted. An alarm can be issued if the count exceeds a defined threshold or a specific bubble exceeds a defined size.

Figure 4B:
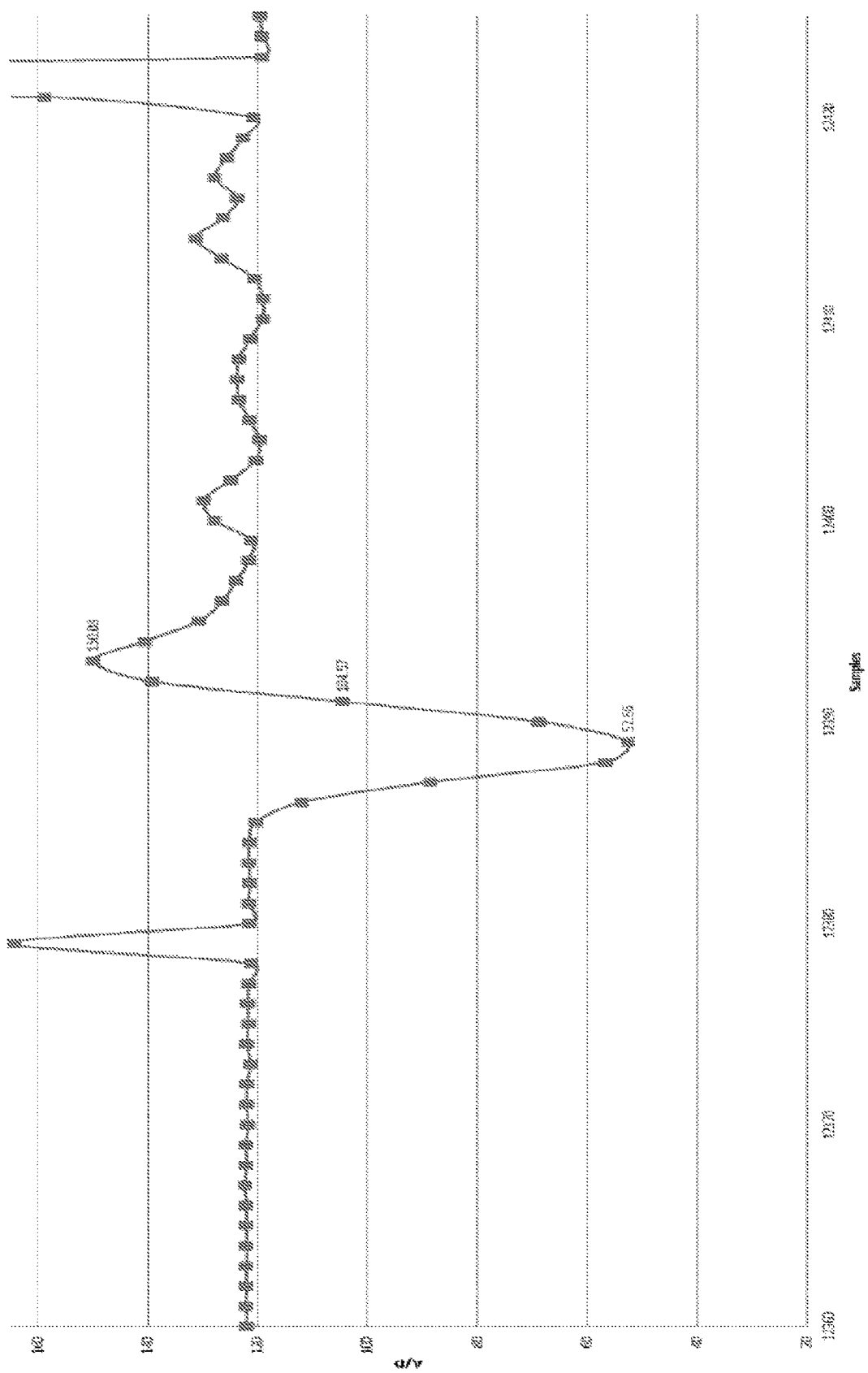
Figure 4C:
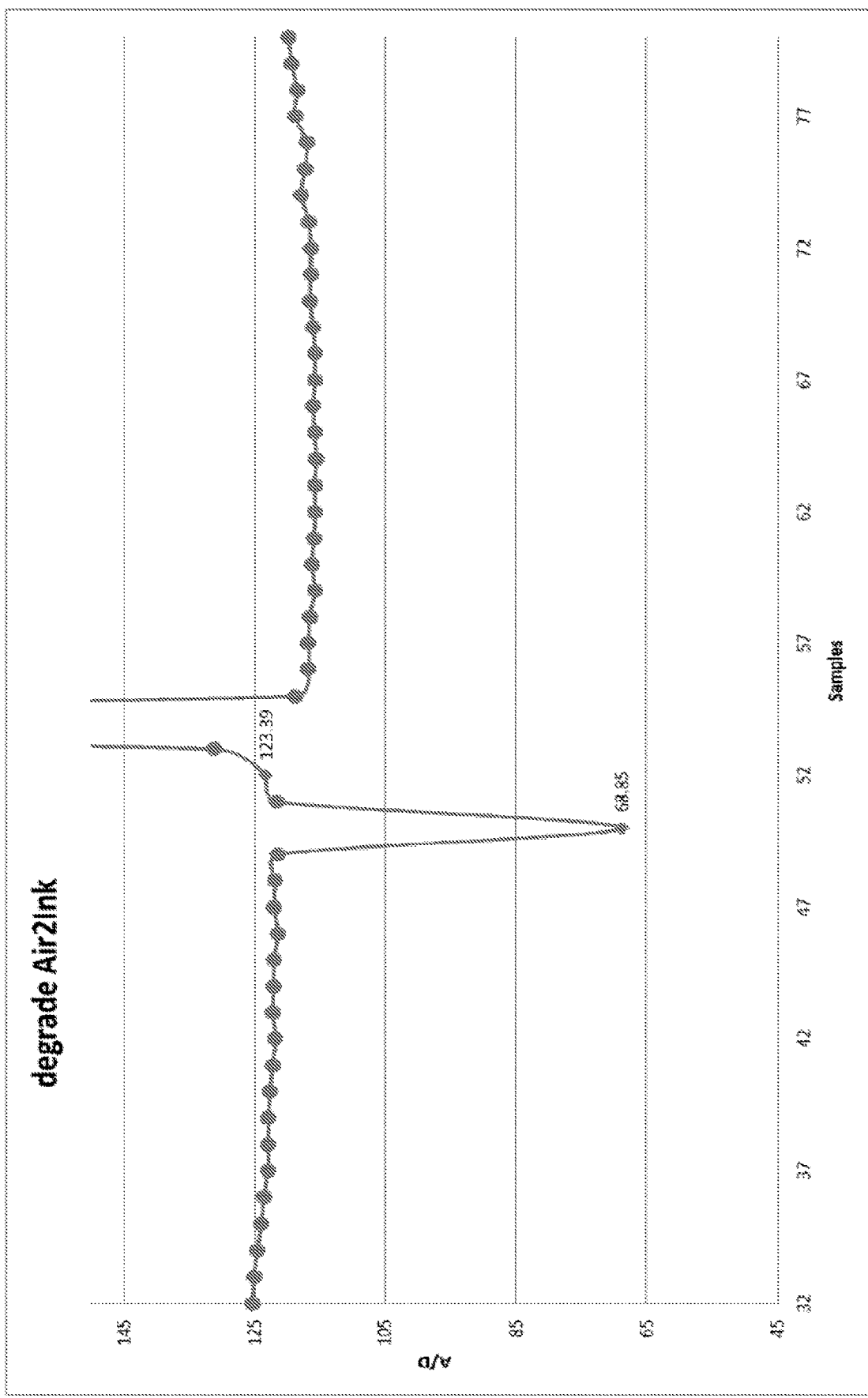

FIGS. 4A-4C present results of exemplary lab experiments designed to identify signals/parameters indicative of boundary conditions within a conduit under observation. In these examples boundary conditions indicative of transition between liquid to air (written liquid2air in the table) or air to liquid (air2liquid), are depicted. It should be understood that the presented experiments are for demonstrative purposes only and thus show only some examples. According to some embodiments, parameters indicative of boundary conditions may depend on the configuration and details of the delivery system, the conduit, the fluid in question, the emitter and light sensor and the distance between them, the sampling methodology and so on. Therefore, parameters may be pre-determined (for example, by experiments such as shown in FIGS. 4A-4C) for each system/configuration, each fluid type, each conduit type, and so on. Further, a calibration of each individual system/device may be performed.

According to some embodiments, a line inspection assembly may be utilized to detect/monitor bubbles within liquid/gel in the line. While the liquid/gel should be delivered to the patient by the medical device the gas/air needs to be monitored and if the gas/air exceeds an allowable volume an alarm should be activated and/or the delivery of the fluid stopped (for example, the medical device therapeutic functionality may be disabled).

Figure 5A:
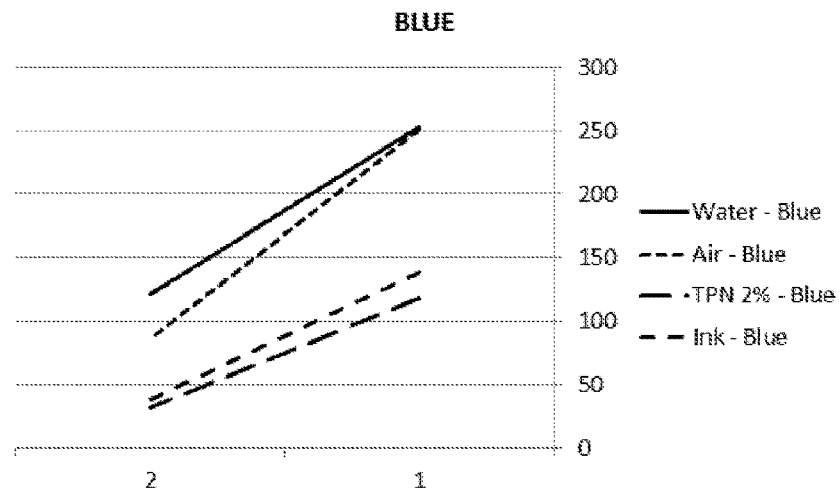
Figure 5B:
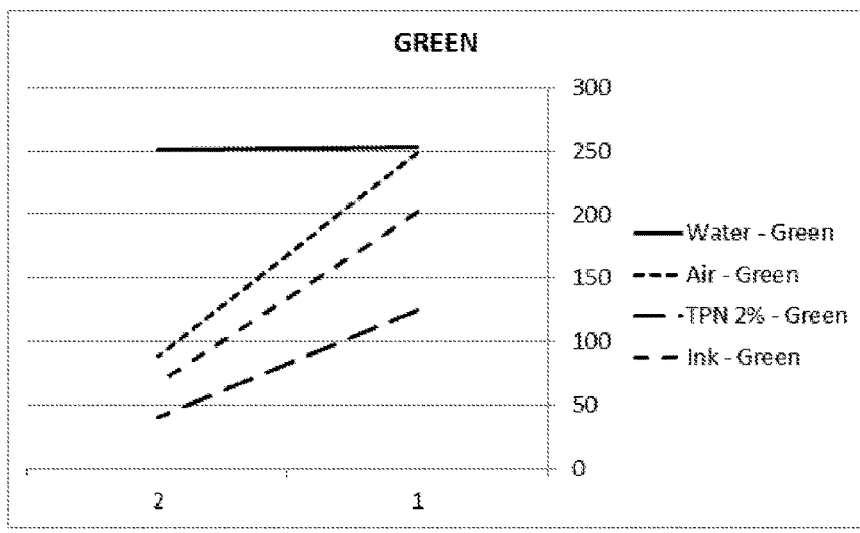
Figure 5C:
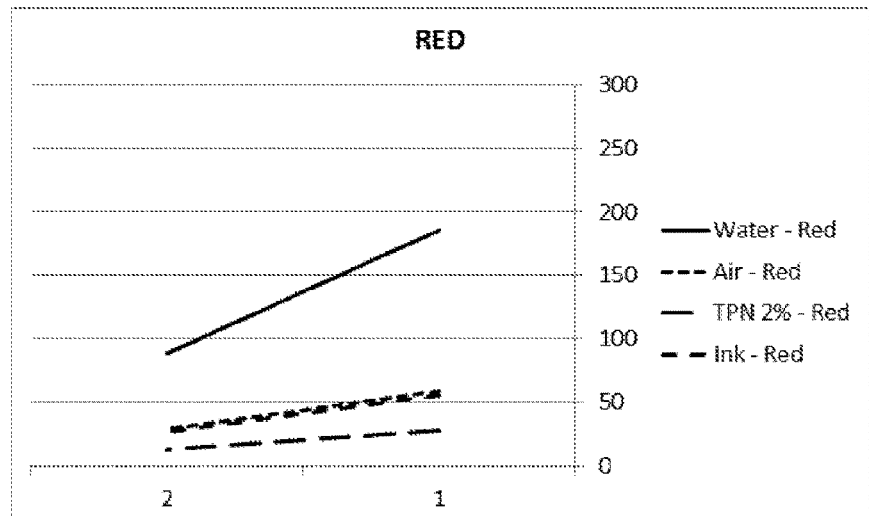
Figure 6A:
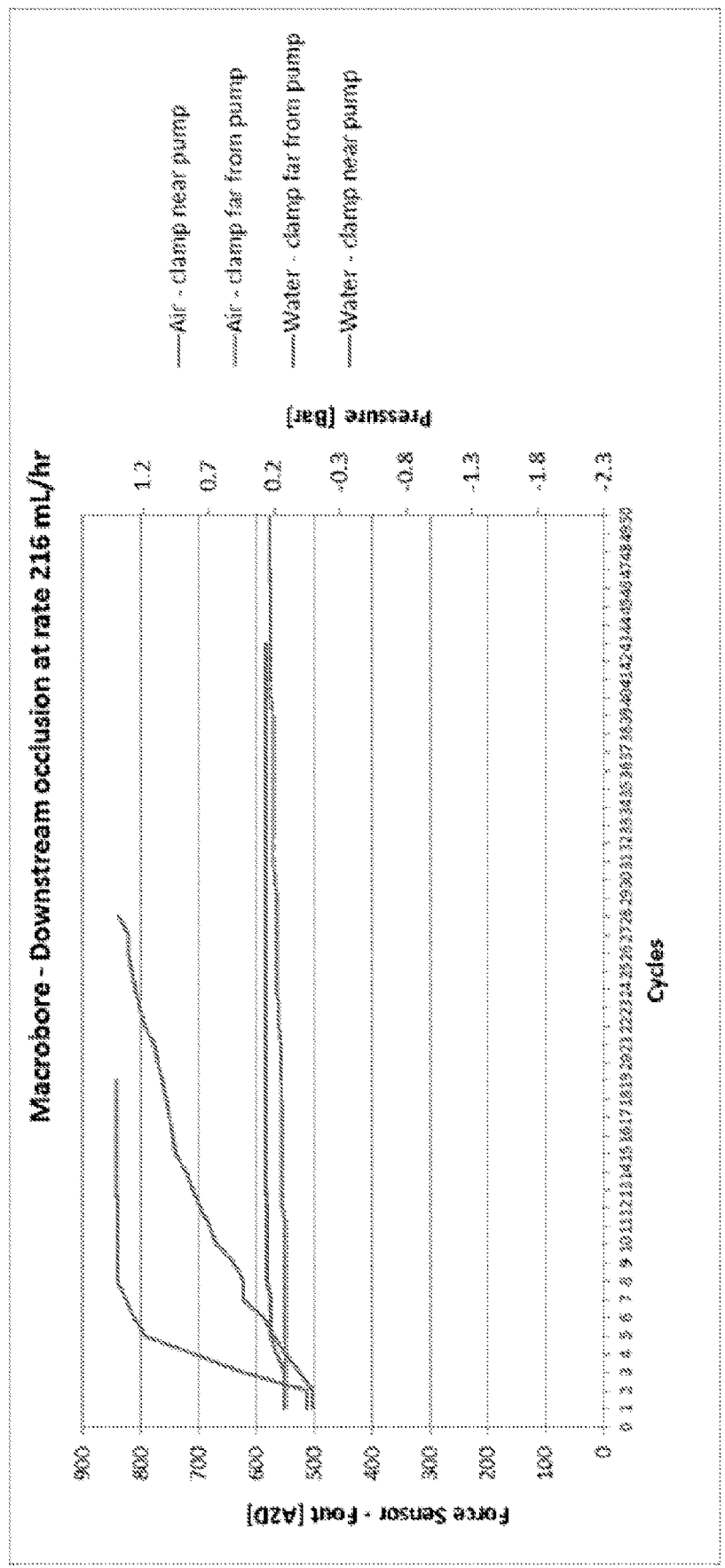
FIGS. 6A-6D present exemplary pressure sensor output results upon the application of a clamp to the line (The different graphs, 6A-6D present examples of results in different conditions), all in accordance with some embodiments of the present invention.
Figure 6B:
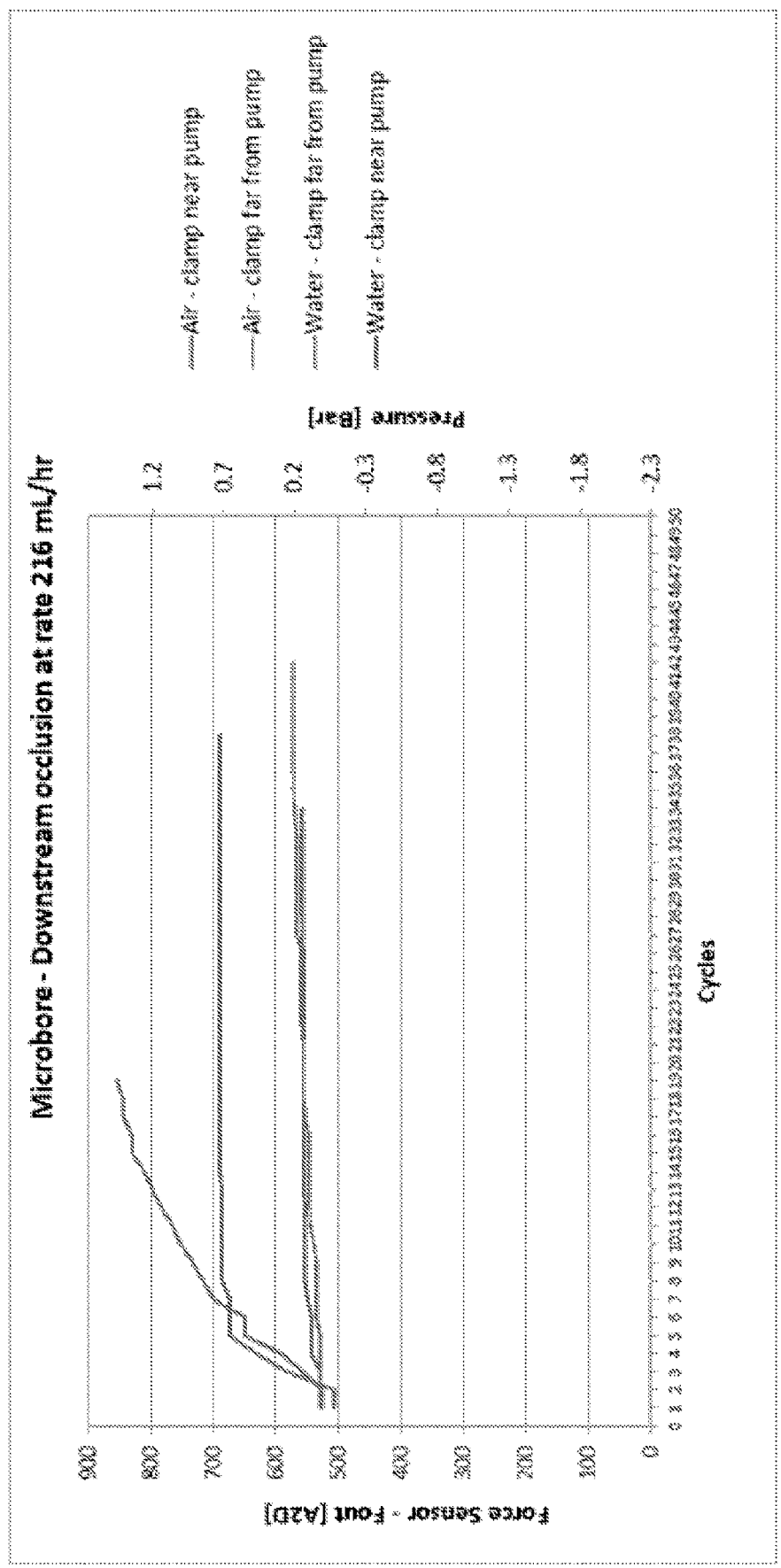
Figure 6C:
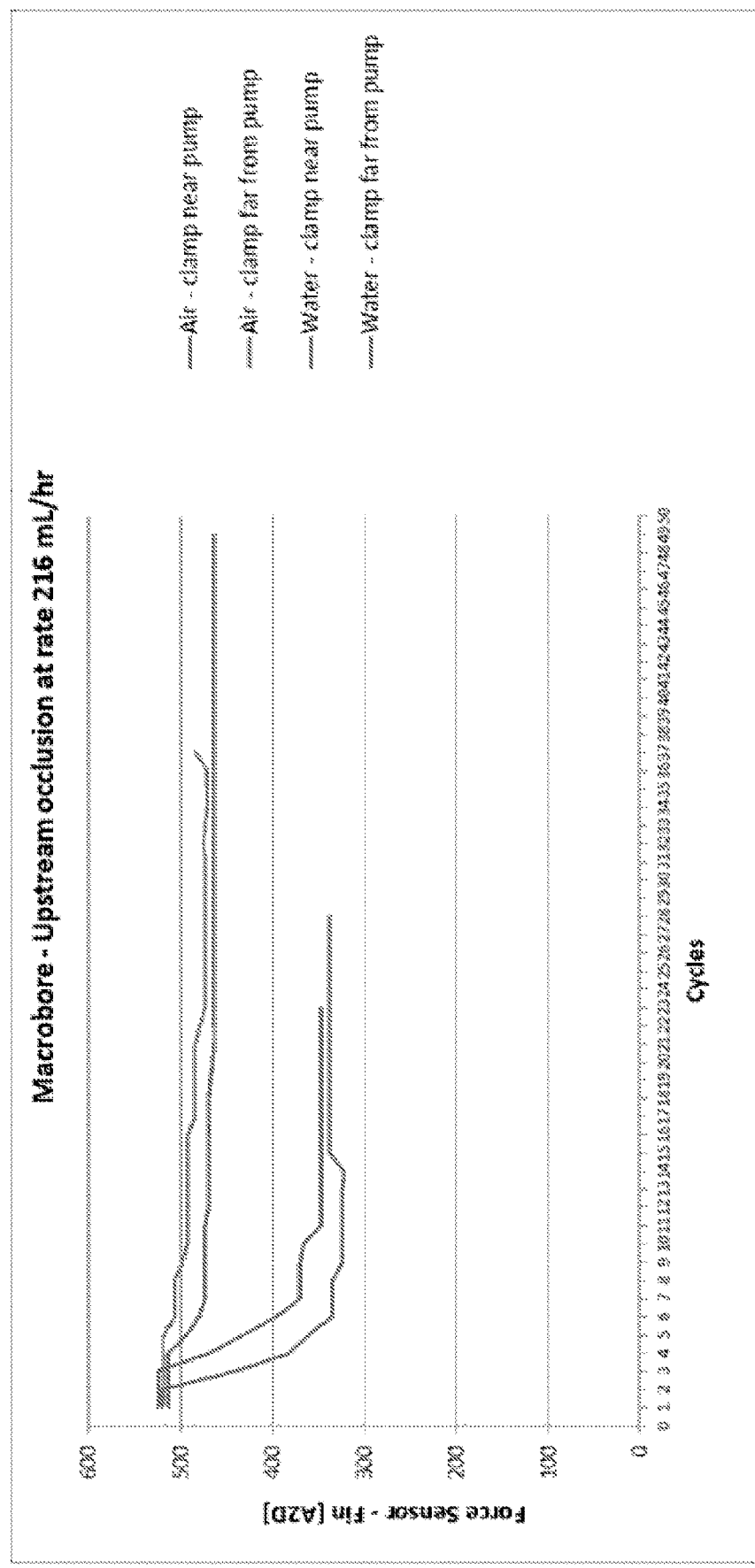
Figure 6D:
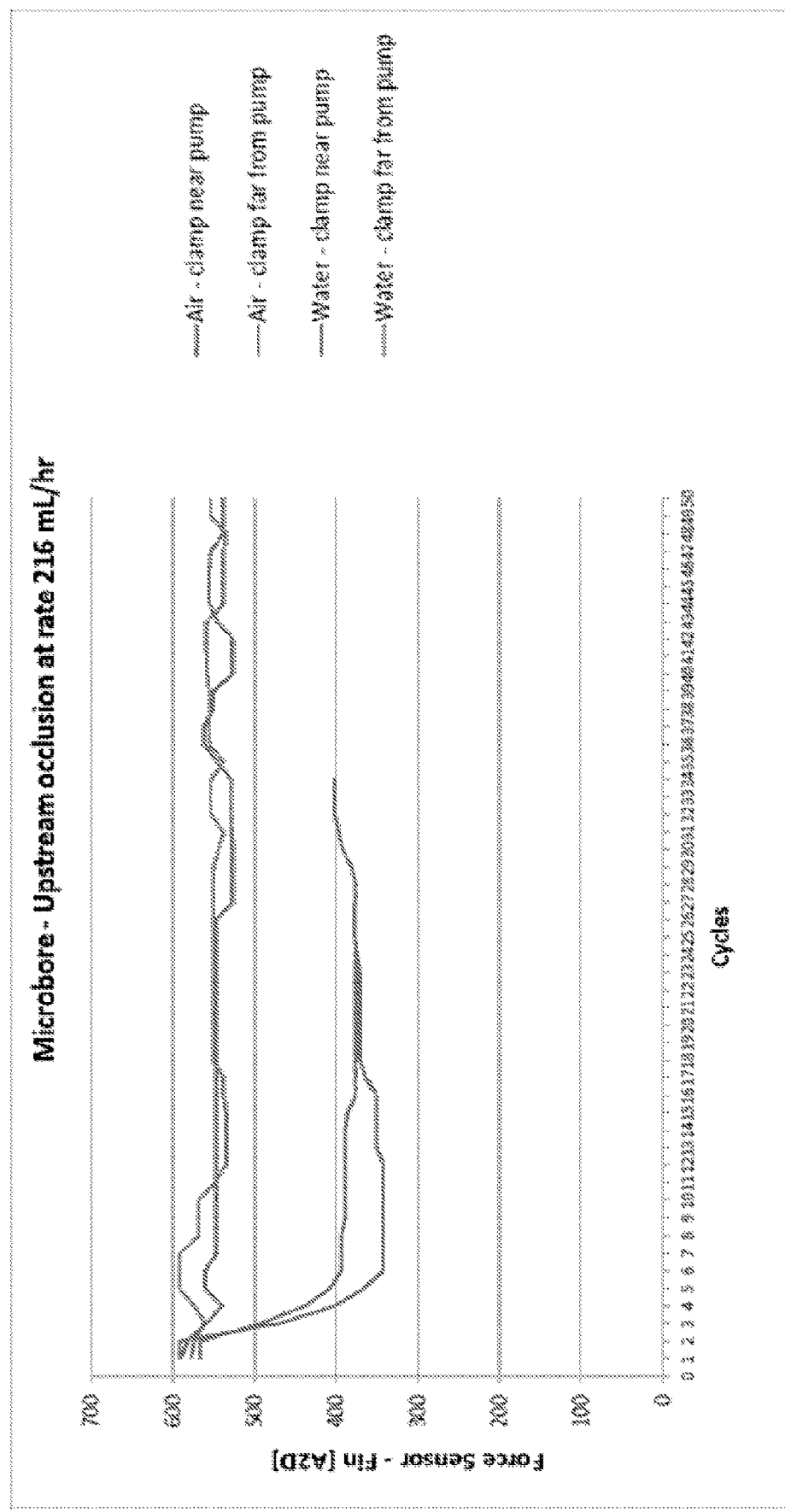

According to some embodiments, a multispectral emitter and associated sensor (such as an RGB emitter+sensor) may be utilized to perform spectral analysis of fluid within a medical conduit. Such systems/devices/methods may emit multiple wavelengths of light and sense an intensity of each wavelength after passing through the fluid. As each substance absorbs light of different wavelengths differently, each substance will have a different spectral signature when present in the conduit. These spectral signatures may be used to identify/classify the fluid within the conduit. Similarly, different fluid types may be detected based on spectral analysis as well as differentiating between liquids and gas/air within the conduit. The method may include characterizing and/or estimating/identifying fluid in the line based on one or more spectroscopic techniques which take into account wavelengths of photons absorbed by each fluid or fluid type. It should be understood that spectral analysis of light passing through a conduit may similarly be used to classify a fluid without full identification of the fluid by comparing the spectral signature sensed to reference spectral signatures, profiles and/or ranges. According to some embodiments, examination of sensor outputs relating to specific wavebands may be used to differentiate between specific fluids. For example, wavelengths between 619 nm and 624 nm (Red) may be used to detect air bubbles in clear liquids due to a significant difference between the measured signals of the two fluids in this optical spectrum, as can be seen in FIG. 5C. Similarly, Wavelengths between 520 nm and 540 nm (Green) may be used to detect air bubbles in opaque liquids, due to a significant difference between the measured signals of the two fluids in this optical spectrum, as can be seen in FIG. 5B. Wavelengths between 460 nm and 480 nm (Blue) may be used to detect air bubbles in semi-transparent liquids due to a significant difference between the measured signals of the two fluids in this optical spectrum, as can be seen in FIG. 5A. Obviously, a cross referencing of multiple wavelengths can be used to classify a fluid as any one of the above discussed 4 categories.

FIGS. 5A-5C present exemplary spectral signatures of different fluids as sensed by exemplary light sensing assemblies such as described herein. FIGS. 5A-5C present signal outputs sensed by an exemplary multi-spectral (RGB) light sensor when sensing a conduit filled with air, when sensing a conduit filled with water, when sensing a conduit filled with TPN 2% (representing an opaque liquid) and when sensing a conduit filled with a mixture of ink and water designed to mimic an Iron Sucrose treatment fluid (representing a semitransparent liquid), wherein FIG. 5A presents the exemplary results in the Blue waveband. FIG. 5B presents the exemplary results in the Green waveband and FIG. 5C presents the exemplary results in the Red waveband all in accordance with some embodiments of the present invention. As can be seen, each fluid affects each wavelength of the light differently, such that the nature, identity, type and/or characteristic of the fluid can be determined based on the output of a light sensor sensing multi-spectral light emitted through the conduit in each wavelength/waveband. Similarly, fluids at different temperatures or having different concentrations of a given substance within them will affect energy/light differently (for example, each substance may absorb different percentages of each wavelength/waveband), allowing for differentiation based on the sensor output. It should be understood that, as the distinction between the effect of different fluids or fluid types upon light passing through them can be used to identify/characterize/classify the fluid within a conduit using a light emitter+sensor, distinctions between the effect of different fluids or fluid types upon another form of energy passing through the fluid can be used to identify/characterize/classify the fluid within a conduit using an appropriate emitter+sensor. Of particular interest is the Iron Sucrose example (represented in FIGS. 5A-5C by the Ink mixture—labeled "Ink"). This fluid affects infra-red light very similarly to air, such that using an IR sensor one cannot reliably distinguish between the two. As can be seen in FIGS. 5B and 5C, light sensor output relating to the Green and Red wave bands also fails to reliably distinguish between the two, as the signals are again similar (the Red more so than the Green). Looking to FIG. 5A, however, it can easily be seen that isolating and analyzing the Blue wave band sensor readings the Iron Sucrose can easily be distinguished from air, being significantly distinct in this wave band.

According to some embodiments, output of a multi-spectral light sensor used to sense multi-spectral light emitted through a medical conduit, as described above, may depend on the configuration and details of the assembly, the conduit, the fluid in question, the emitter and light sensor and the distance between them and so on. Therefore, parameters may be pre-determined (for example, by experiments such as shown in FIGS. 5A-5C) for each system/configuration, each fluid type, each conduit type and so on. Further, a calibration of each individual system/device may be performed. According to some embodiments, a spectral signature of a substance may be identifiable regardless of some modifications of configuration and components of the sensing system, thereby reducing the need for calibration and pre-testing of each system.

According to some embodiments there may be provided a sensor adapted to sense pressure/force within a medical delivery system conduit, as shown in FIGS. 13A-15B. According to further embodiments, the pressure/force sensor may function in combination with a clamp adapted to partially or completely obstruct flow of fluid through the conduit and/or apply pressure/force to the conduit, as shown in the Figures. According to some embodiments, by measuring the change of pressure and/or rate of change of pressure within the conduit upon applying/releasing the clamp, the nature of the fluid within the conduit and/or the amounts of liquid/gas/air within the conduit may be determined. This may be done due to the fact that the changes in pressure resulting from applying and/or releasing the clamp depend on the physical characteristics of the fluid within the conduit and its pressure.

Figure 8:
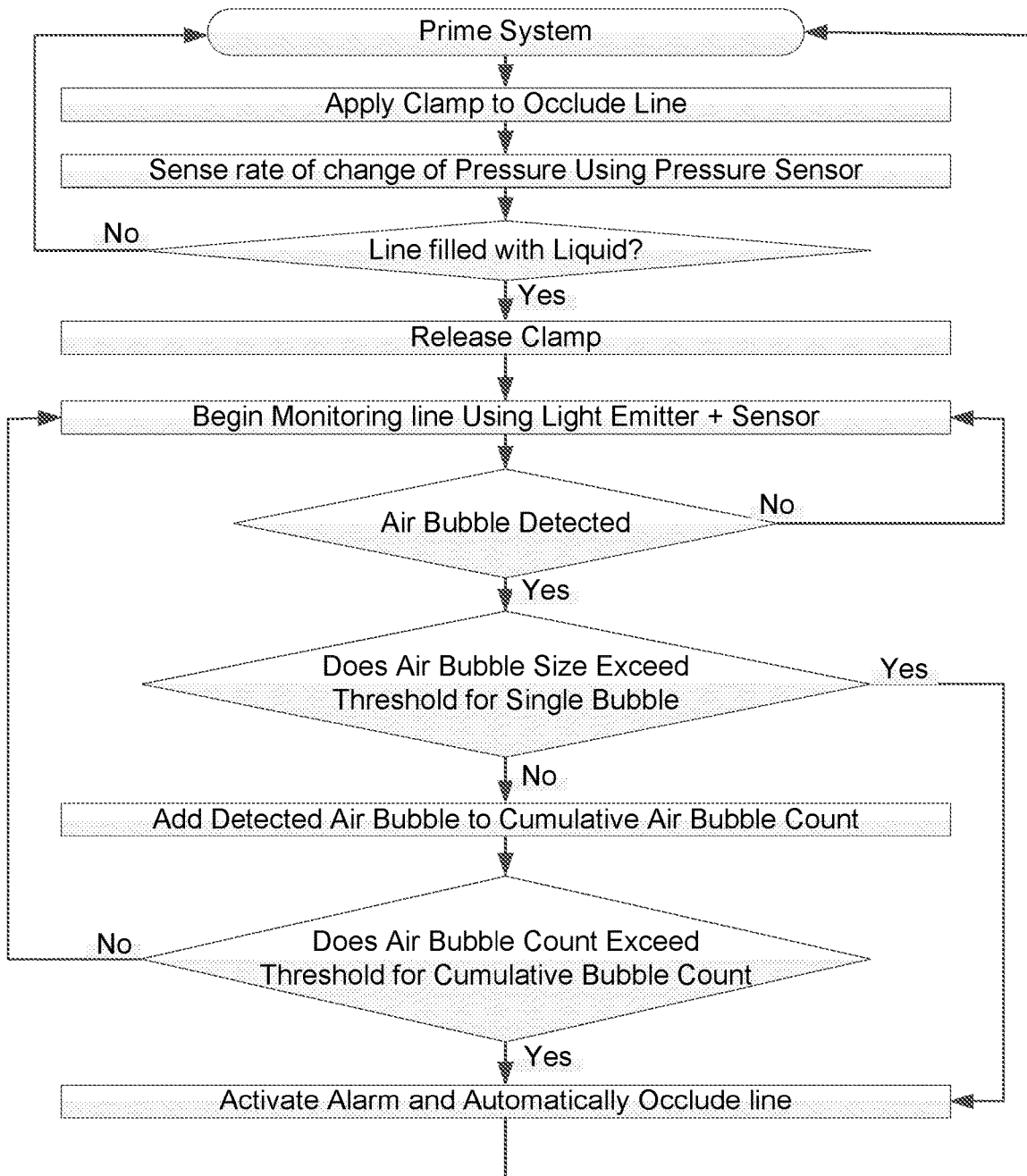
FIG. 8 is a flowchart presenting steps of operation of an exemplary medical conduit monitoring system including a pressure sensor and clamp assembly and a light sensing assembly, showing the use of the clamp+pressure sensor to verify priming and/or the presence of liquid in the conduit prior to commencement of monitoring by the light sensor, all in accordance with some embodiments of the present invention.
Figure 9:
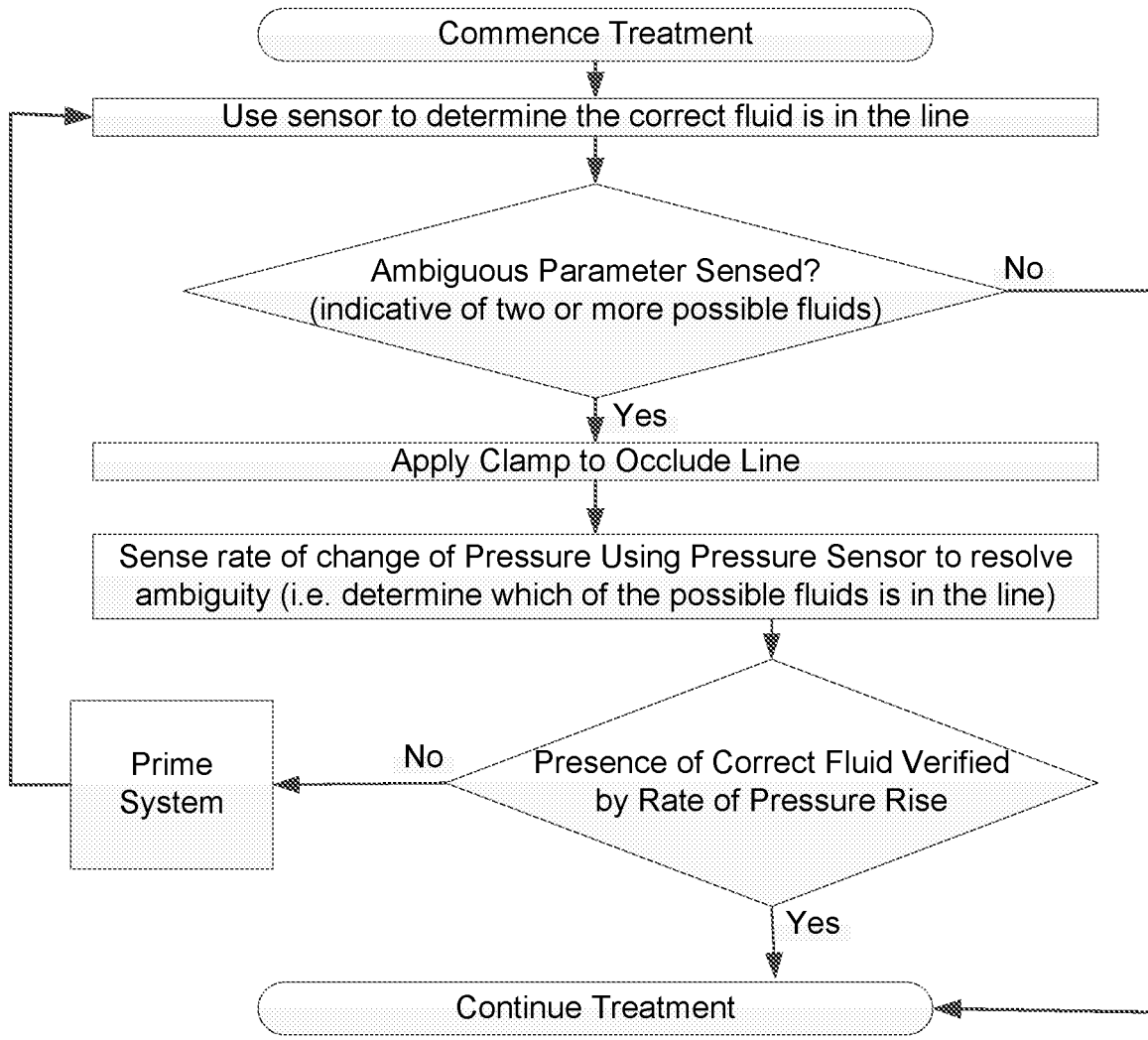
FIG. 9 is a flowchart presenting steps of operation of an exemplary medical conduit monitoring system including a pressure sensor and clamp assembly and another sensing assembly, showing the use of the clamp+pressure sensor to resolve ambiguous and/or verify measurements/output of the other sensor assembly, all in accordance with some embodiments of the present invention.

According to some embodiments, a medical line sensing assembly may include a pressure inducing/crimping/pinching/occluding device or circuitry (for example, a clamp) and a force sensor (shown in FIGS. 13A-15B). In this configuration the assembly may be utilized to detect if mostly liquid or air/gas are in the line, assess a percentage/density of gas/air/liquid in the line and/or otherwise identify or quantify the substance in the line. In order to perform a measurement, the clamp may first be closed so that the line is disrupted/obstructed and then the signal processing unit may analyze the signal received from the line inspection assembly pressure/force sensor. It should be understood that the signal will depend on the nature of the fluid in the conduit, such that different fluids and/or their percentages in conduit, may be distinguishable. For example, liquid may cause pressure to build more quickly and to a higher value than gas/air. Therefore, by applying the clamp and then measuring the rise in pressure, a conduit filled with liquid can be differentiated from a conduit mostly or partially filled with air, as the pressure will rise much more quickly in the case that the conduit is filled with liquid. Typically such an assembly and method may be utilized to confirm that there is liquid in the line, to confirm priming has been done or to receive verification that the line is filled with liquid. Verification that the line is filled may be utilized for example in conjunction with the methods presented in FIGS. 3C-3D. Optionally, a patient may be disconnected from the line before carrying out the method. It is understood that the pressure inducing device may be downstream or upstream to the medical device. According to some embodiments, inducing pressure in a line to detect if there is substantially liquid or substantially gas may be utilized if an assembly including an emitter and a sensor are incapable of differentiating between the two (as shown in FIG. 9), for example some fluids have a spectral characterization that is undetectable by an IR emitter. Additional configurations where inducing pressure to differentiate between air and gas are understood, for example for added safety to confirm priming or provide an initial state for the system (as shown in FIG. 8). Some embodiments of the present invention including a force sensor and clamp may further include one or more physical interfaces for positioning the clamp and/or pressure sensor in relation to the conduit so as to perform their function, as shown in the figures. The interface may be integral to the medical device or a separate component adapted to attach/mount on the device or conduit. The interface may further include physical and/or electronic adaptations to facilitate operation of the force sensor and clamp. According to some embodiments, application of the clamp/pinching-element/occluding-element may be actuated automatically by an associated processor, possibly using an associated actuator, and/or manually. In manual embodiments, an associated display or other output device may be provided so as to allow the processor to signal a user to apply the clamp.

FIGS. 6A-6D present exemplary line pressure sensor output results upon the application of a clamp to the line. The different graphs present results in different conditions. It should be understood that the presented experiments are for demonstrative purposes only and thus show only some examples. As can be seen, the rate of pressure rise in liquid greatly exceeds the rate of rise in gas/air. Clearly, by measuring the rate of rise in pressure after applying the clamp, a conduit filled with air can be differentiated from a conduit filled with liquid. Further, by performing a series of measurements of pressure rise in the conduit with different percentages of air and liquid in the conduit, reference pressure rise parameters for each percentage of air/gas to liquid can be established. Further, a formula for pressure rise parameters for each percentage of air/gas to liquid can be established for each system configuration. Accordingly, the line pressure sensor output may be used to accurately assess a percentage of air/gas within the conduit. Similarly, different liquids or gases within the conduit may be identified based on the measured rise in pressure by comparing to reference parameters previously measured, or a temperature/pressure of the fluid within the conduit may thus be determined.

According to some embodiments, rate of rise of pressure within a medical conduit upon application of a clamp may depend on the configuration and details of the delivery system, the conduit, the fluid in question, the clamp and pressure sensor and the distance between them and so on. Therefore, parameters may be pre-determined (for example, by experiments such as shown in FIGS. 6A-6D) for each system/configuration, each fluid type, each conduit type, and so on. Further, a calibration of each individual system/device may be performed.

It should be understood that drop in pressure upon release of a clamp may also be used in a similar manner, alone or in conjunction with measurement of rise in pressure upon application of the clamp (for example, for verification).

Exemplary Parameters Affecting Pressure Build-Up:

Set Length—the longer the set, the slower the pressure build in the set.

Set Type—pressure build behaves differently in different sets (narrow sets are typically characterized by higher pressure).

Occlusion location—the further the occlusion is from the sensor—the longer it will take for the pressure to accumulate.

Treatment Rate—the slower the rate, the slower the pressure build in the set.

Pump pressure threshold parameters—the higher the pump pressure threshold—the longer it will take to reach the threshold (pressure build up takes time).

According to some embodiments of the present invention, a pressure/force sensor assembly including a clamp designed to measure the rise and fall of pressure within a medical conduit upon application/release of the clamp, as described herein, may be implemented in combination with other conduit/line sensing assemblies to verify and/or complement their operation. For example, as shown in FIG. 8, a clamp+force/pressure assembly may be used to verify/detect whether an associated medical delivery system has been primed (i.e. whether the conduit(s) are filled with liquid), after which a light sensing assembly, such as described herein, may begin monitoring the line under the knowledge that the initial reading is liquid. In another example, upon determination by another sensor that an unacceptable level of air is present in the conduit, the clamp+force/pressure assembly may be used to verify the determination. In a further example, as shown in FIG. 9, upon receiving an ambiguous reading from an associated sensor, indicating more than one possible substance within the line, a clamp+force/pressure assembly may be used to resolve the ambiguity. For example, iron sucrose is difficult to differentiate from air using a light sensor (the readings are similar). Therefore, in a relevant delivery system, a reading by a light sensor indicating either iron sucrose or air in the conduit, a clamp+force/pressure assembly may be used to distinguish between the two. In yet another example, pressure change rate following a clamp release/activation may be used to assist in determining and/or verifying the identification and/or classification of a fluid within a conduit based on another sensor type, as also shown in FIG. 9.

According to some embodiments of the present invention, there may be provided a processor/processing-circuitry adapted to analyze output from one or more sensors functionally associated with a medical fluid delivery system/device, to determine one or more of:

a. whether the conduit is filled with gas or liquid—as described herein, the determination whether the conduit is filled with gas/air or liquid may be derived from measurements of pressure within the conduit and/or changes in pressure in response to the application and/or release of pressure/clamping to the conduit. The nature of the fluid within the conduit may also be determined from output of a light sensor associated with the conduit, i.e. based on parameters of light having passed through the fluid. According to further embodiments, both sensing techniques may be used alternatively and/or in combination. For example, the nature of the fluid may regularly be determined based on light sensing and in the event the light sensing is inconclusive (such as in the Iron Sucrose case), at critical moments and/or upon the detection of critical conditions, pressure/clamping may be applied and the associated force/pressure measurements made;

b. the identity of the fluid in the conduit and/or characteristics thereof—as described herein, spectral analysis of light having passed through the conduit may be used to determine the identity of the fluid within the conduit and/or to determine one or more characteristics of the fluid;

c. identify air bubbles and their size and quantity—as described herein, analysis of light having passed through the conduit may be used to identify air bubbles within a liquid flowing through the conduit and determine their size. According to some embodiments, air bubbles may be detected and identified by detecting changes in the parameters of light having passed through the fluid which are indicative of transition between substances (boundary conditions); and d. whether any given air bubble is static or dynamic—as described herein, by measuring one or more of the above parameters over time and determining the rate of change of the relevant parameter, the movement, or lack thereof, of the given air bubble may be determined. Further, once a static air bubble is detected it may be monitored to detect if it becomes dynamic.

According to some embodiments, a system including one or more medical line sensors and/or output from the one or more medical line sensors and a micro controller/air-bubble-analysis circuit may be configured to analyze sensor output data to assess the mobility of detected air bubbles and differentiate between static and dynamic air bubbles. The system may trigger an alarm if a dynamic air bubble (or an accumulation of dynamic air bubbles) above a clinical threshold is detected.

Figure 10:
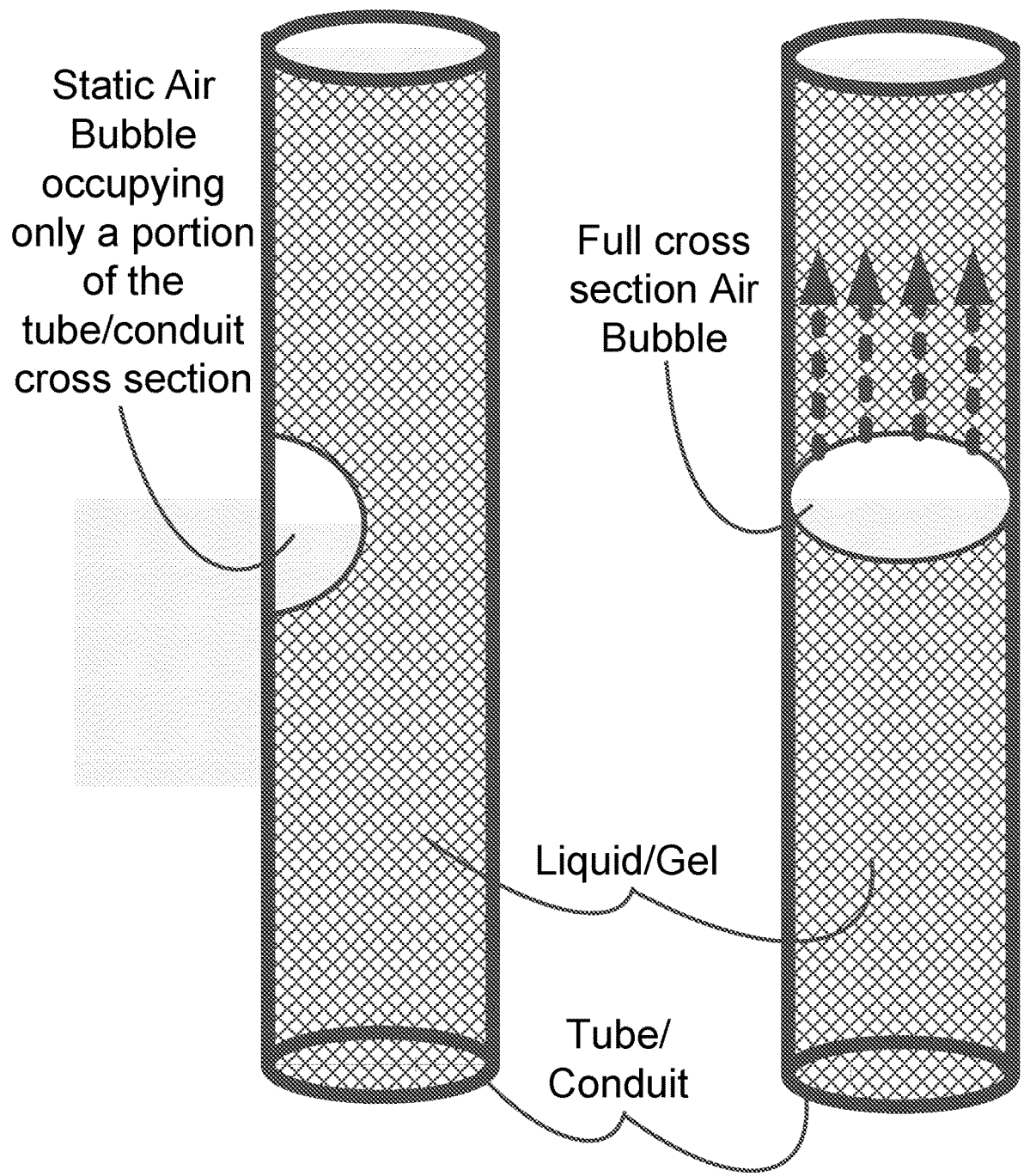
FIG. 10 is an illustration of exemplary static and dynamic air bubbles within conduits, showing an exemplary dynamic air bubble occupying the full cross section of the conduit it is within, in contrast to an exemplary static air bubble occupying only a portion of the conduit it is within, all in accordance with some embodiments of the present invention.

Sometimes small bubbles may get stuck in the conduit (as shown in FIG. 10). Experiments have shown that small stuck bubbles within the field of view of the bubble detector can cause AIL (Air in Line) alarms even when there aren't any viable clinical air bubbles (dynamic air bubbles that may travel downstream to the patient line) that can harm the patient. In some cases, the static "stuck" bubble is not a full cross section bubble; it occupies only part of a tube diameter (see FIG. 10) or conduit cross section. It may remain static as long as it is partial. It is understood that if a full cross-section air bubble moves through the tube, it carries the smaller bubbles with it.

According to some embodiments static air bubbles which are not moving downstream in a direction of a patient line and/or are "stuck" in a sensor's view may be differentiated from dynamic air bubbles which are moving downstream. Dynamic air bubbles may be monitored so that when their quantity/size exceeds a predefined threshold an alarm may be triggered and/or an associated medical device may be deactivated/disengaged. By differentiating between the static and dynamic air bubbles unneeded alarms are avoided, for example when an air bubble is stuck in the view/reception of a sensor. Prior art solutions that do not differentiate between dynamic and static air bubbles may emit a clinically unnecessary alarm. According to some embodiments static air bubbles may be monitored to detect/notify/relay if a change in their characterization occurs/if they transition/turn into dynamic air bubbles (For example, a larger air bubble carries them downstream or otherwise).

Figure 11A:
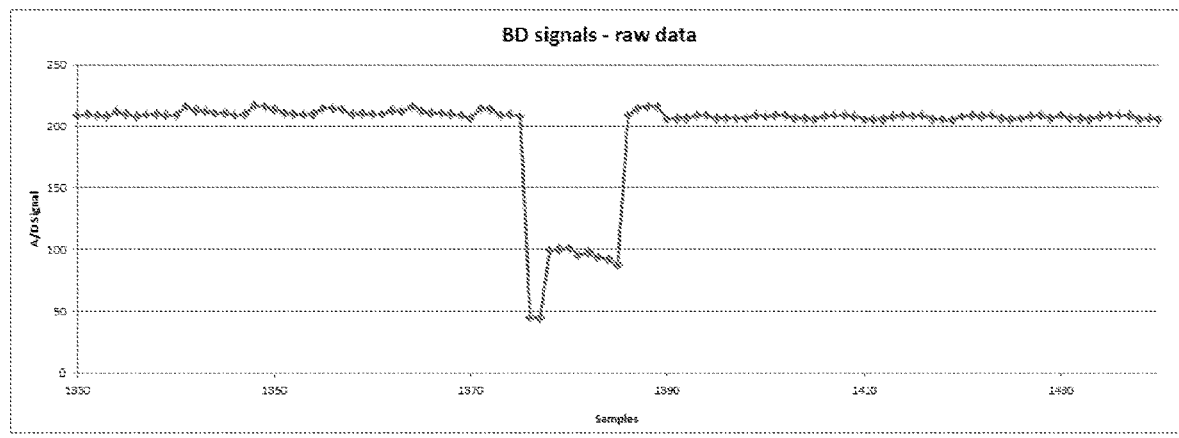
FIGS. 11A-11E are exemplary graphs of exemplary output of an exemplary sensor sensing parameters of a fluid within a conduit, wherein FIG. 11A includes a graph comprised of a series of sensor outputs measured during the passing of an exemplary dynamic/moving air bubble, FIG. 11B also includes a graph comprised of a series of sensor outputs measured during the passing of an exemplary dynamic/moving air bubble, FIG. 11C includes a graph comprised of a series of sensor outputs measured during the passing of an exemplary static air bubble, FIG. 11D also includes a graph comprised of a series of sensor outputs measured during the passing of an exemplary static air bubble and FIG. 11E includes a graph comprised of a series of sensor outputs measured over a long series of pump cycles and as multiple static and dynamic air bubbles pass through the monitored conduit, all in accordance with some embodiments of the present invention. Attention should be drawn to the difference in the scale of the X axis between the different Figures.
Figure 11B:
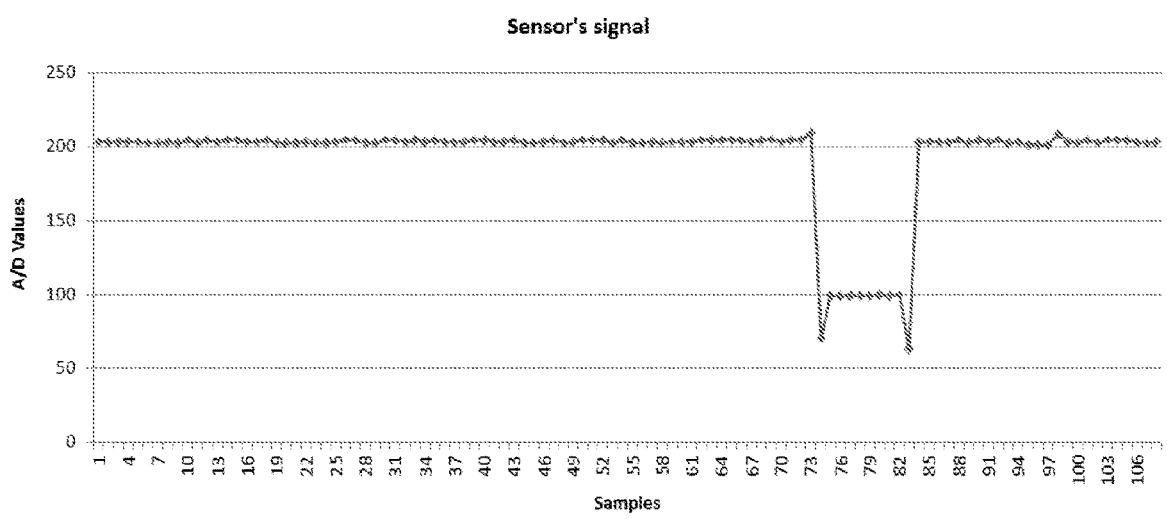
Figure 11C:
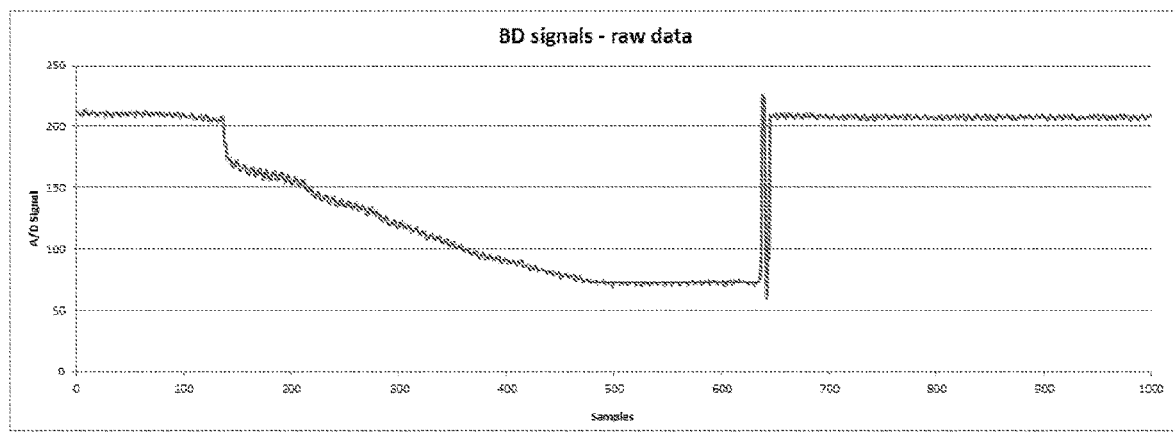
Figure 11D:
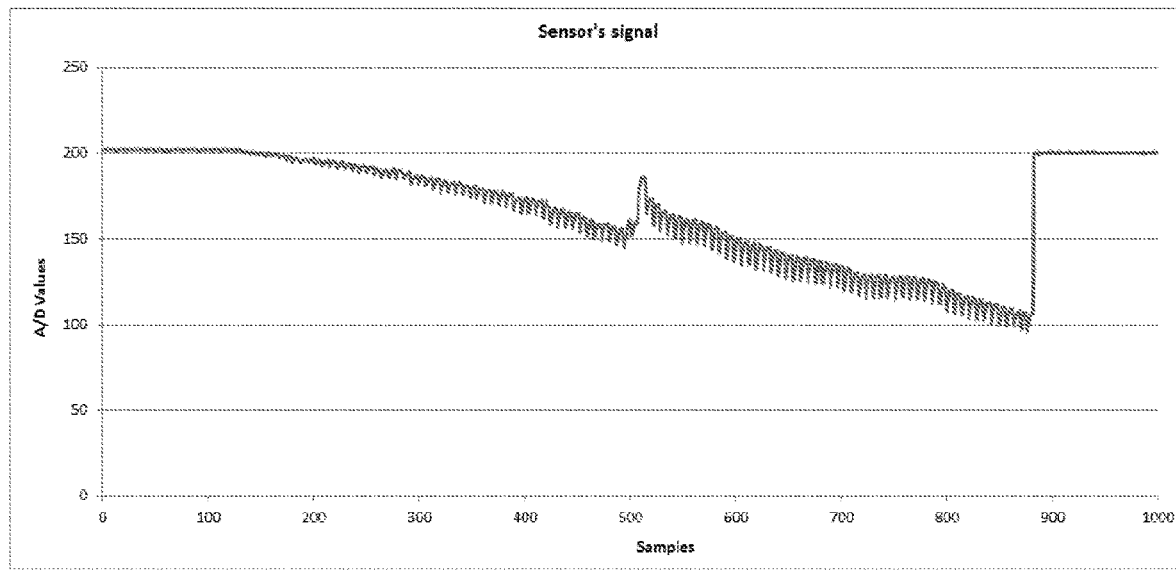
Figure 11E:
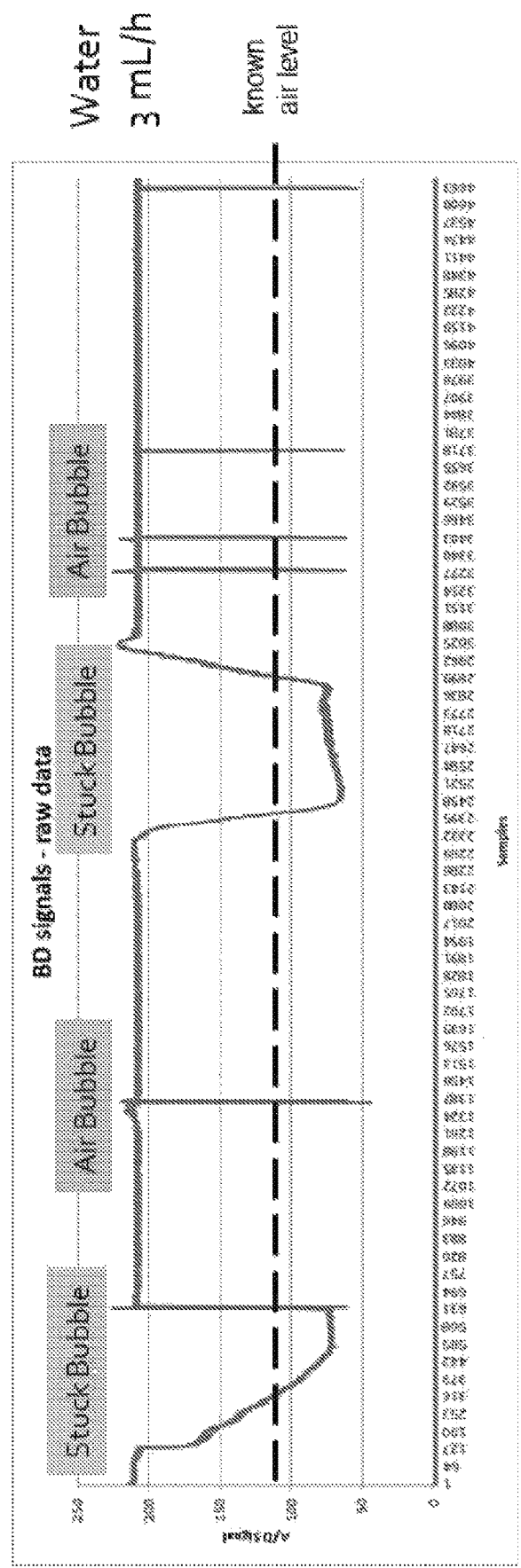

According to some embodiments, sensor output associated with dynamic air bubbles (shown in FIGS. 11A, 11B and 11E) may be distinct from sensor output associated with static air bubbles (shown in FIGS. 11C, 11D and 11E). The sensor output characteristics may also be dependent on the conduit configuration, signal processing, sensor characteristics, the type of fluid flowing through the conduit and more. The sensor may be any type of medical line sensor discussed in this application or any other form of medical line sensor adapted to detect and/or measure air-bubbles within the medical line (for example, a light sensor such as an infra-red (IR) sensor and/or an ultra-sonic sensor).

A sensor output signal for a dynamic air bubble is very distinct from a sensor output signal for a static air bubble. This can clearly be seen by comparing the signals indicative of dynamic air bubbles shown in FIGS. 11A and 11B to the signals indicative of static air bubbles shown in FIGS. 11C and 11D (attention should be made to the difference in scales of the X axis in these figures). The distinction can also be seen in FIG. 11E which shown both on the same scale. Accordingly, by analysis of a sensor output relating to an air bubble and comparison to typical dynamic and/or static bubble sensor output signals, an assessment of mobility of an air bubble may be performed.

According to some embodiments, an output of an air-bubble sensing sensor may be a digital quantification of the sensed signal as a function of the sample number/time. Sensing of a dynamic air bubble may therefore be characterized by certain signal parameters, sets of parameters and/or patterns, such as a quick transition in the output (defined by a certain slope; for example decrease of 50A/D within 4 samples), then stabilization within a defined range associated with an air bubble and possibly followed by another relatively quick transition in the output. Sensing of a static air bubble may therefore be characterized by a slower transition in the sensor output (defined by a second slope for example a slop that decreases or increases over hundreds of samples), where the output continuously changes in the same direction and/or may reach a pseudo-stabilization. All this can clearly be seen in FIGS. 11A-11E.

In other words, static air bubbles may be differentiated from dynamic air bubbles based on a rate of change of sensor output when detecting the relevant bubble. Further, rate of mobility of an air bubble may be similarly determined. Yet further, by analyzing an amount of time a relevant sensor output is detected (a duration of the detection) the mobility and speed of an air bubble may be analyzed.

For example calculating a filter for a relevant sensor signals may=(previous filter*7+(Previous A/D value−Current A/D value))/8; Filter slope=(Filter slope*7+(previous filter signal−current filter signal))/8; filter slope<0.1 are typical of static bubble).

Different thresholds may be used in different systems to differentiate static air bubbles from dynamic air bubbles. Similarly, different uses may require different thresholds. For example, different thresholds may be used for epidural delivery than for IV delivery.

According to some embodiments, parameters indicative of static/dynamic air bubbles may depend on the configuration and details of the delivery system, the conduit, the fluid in question, the type of sensor being used and so on. Therefore, parameters may be pre-determined for each system/configuration, each fluid type, each conduit type, etc. Further, a calibration of each individual system/device may be performed.

Typically, the sensor output may be sampled several times during each cycle of the associated medical device. It is further understood that the sensor output signal may be dependent on the fluid type and/or sensor type so that the first slope, second slope and more may also be dependent on a detection of fluid type (clear, opaque or otherwise). Analysis may also be carried out on frequencies and/or periodicity of the signal.

Figure 7:
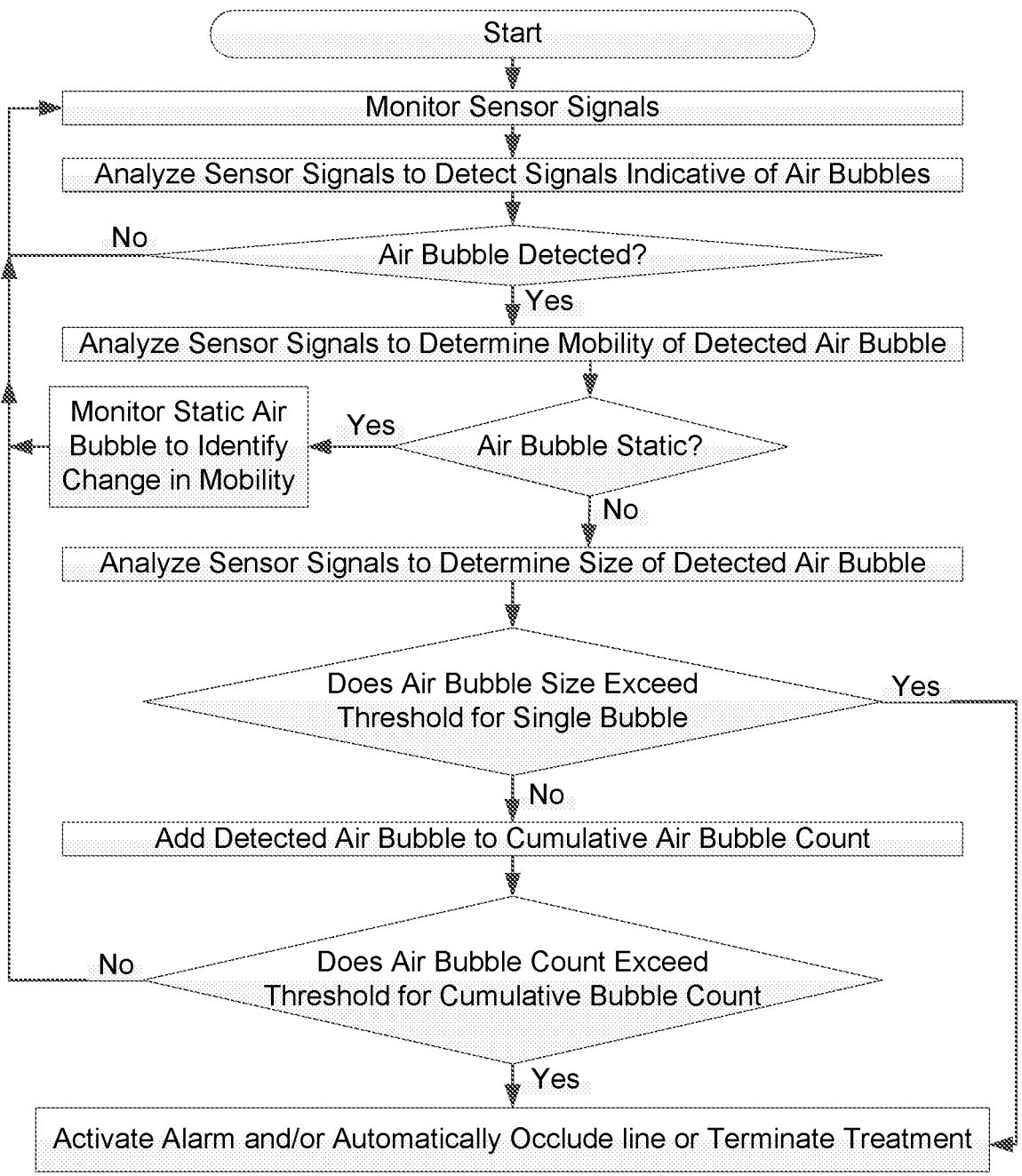
FIG. 7 is a flowchart presenting steps of operation of exemplary monitoring of air bubbles within a medical conduit, including factoring their mobility, all in accordance with some embodiments of the present invention.
Figure 14A:
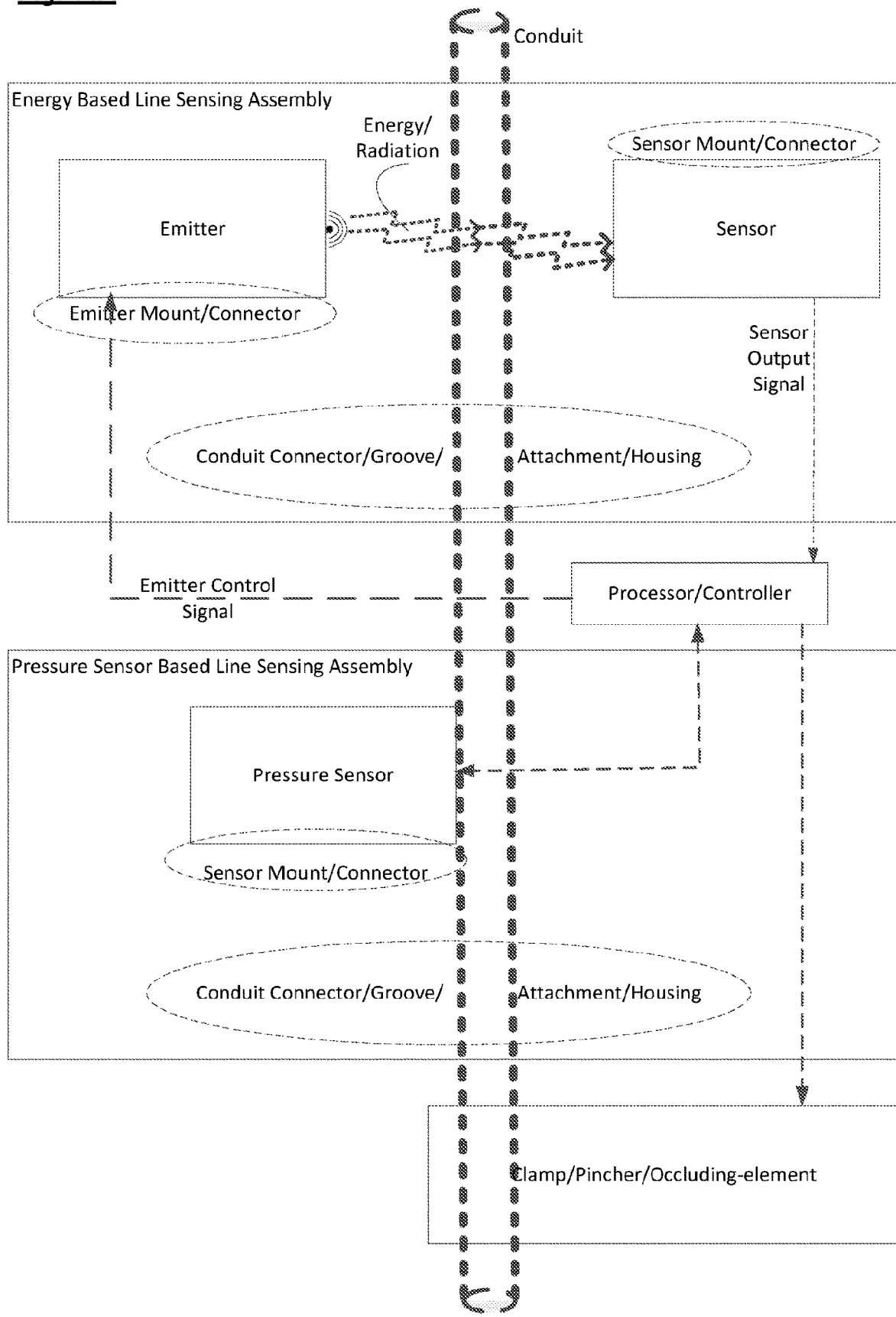
Figure 14B:
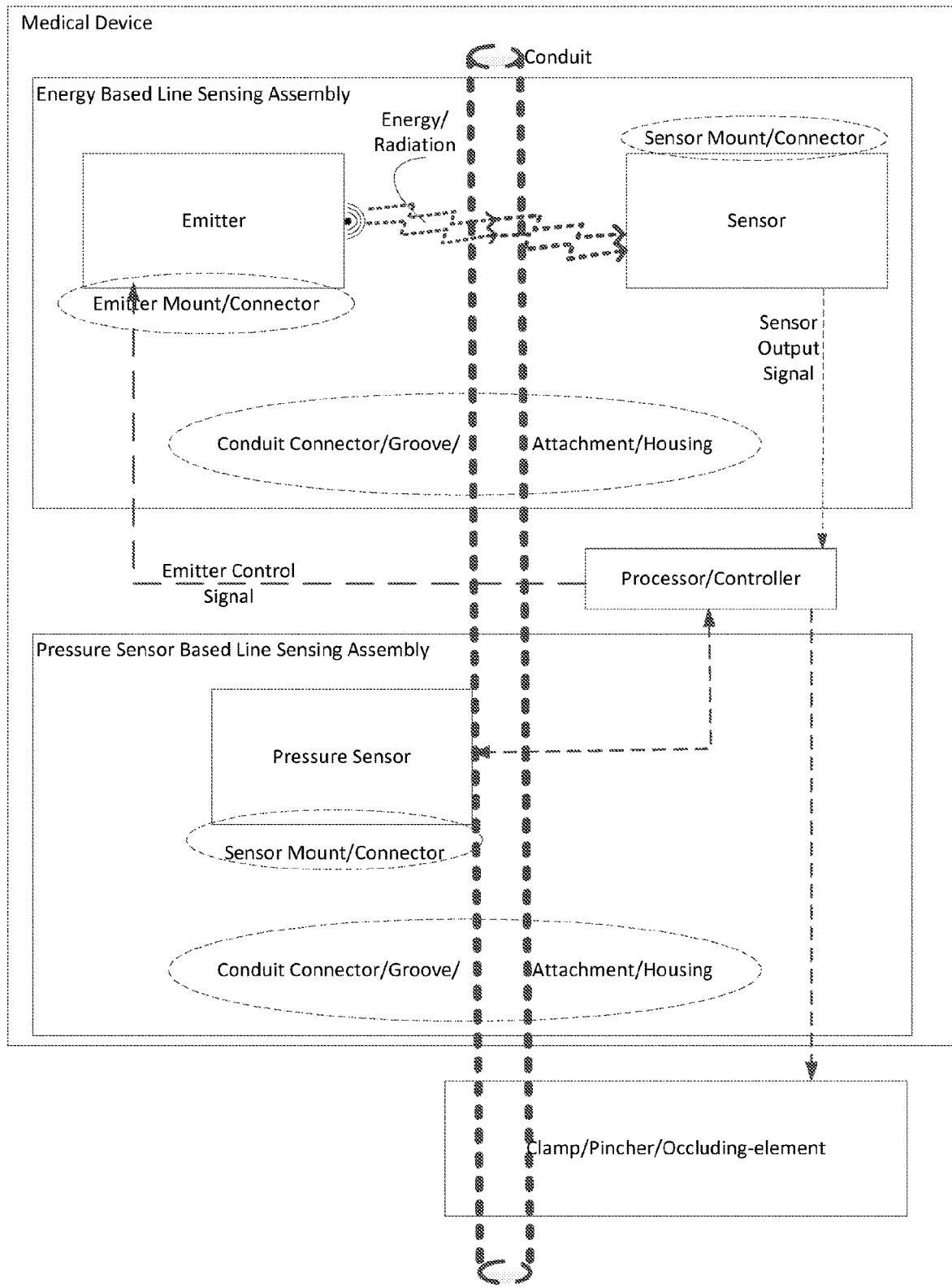
Figure 15A:
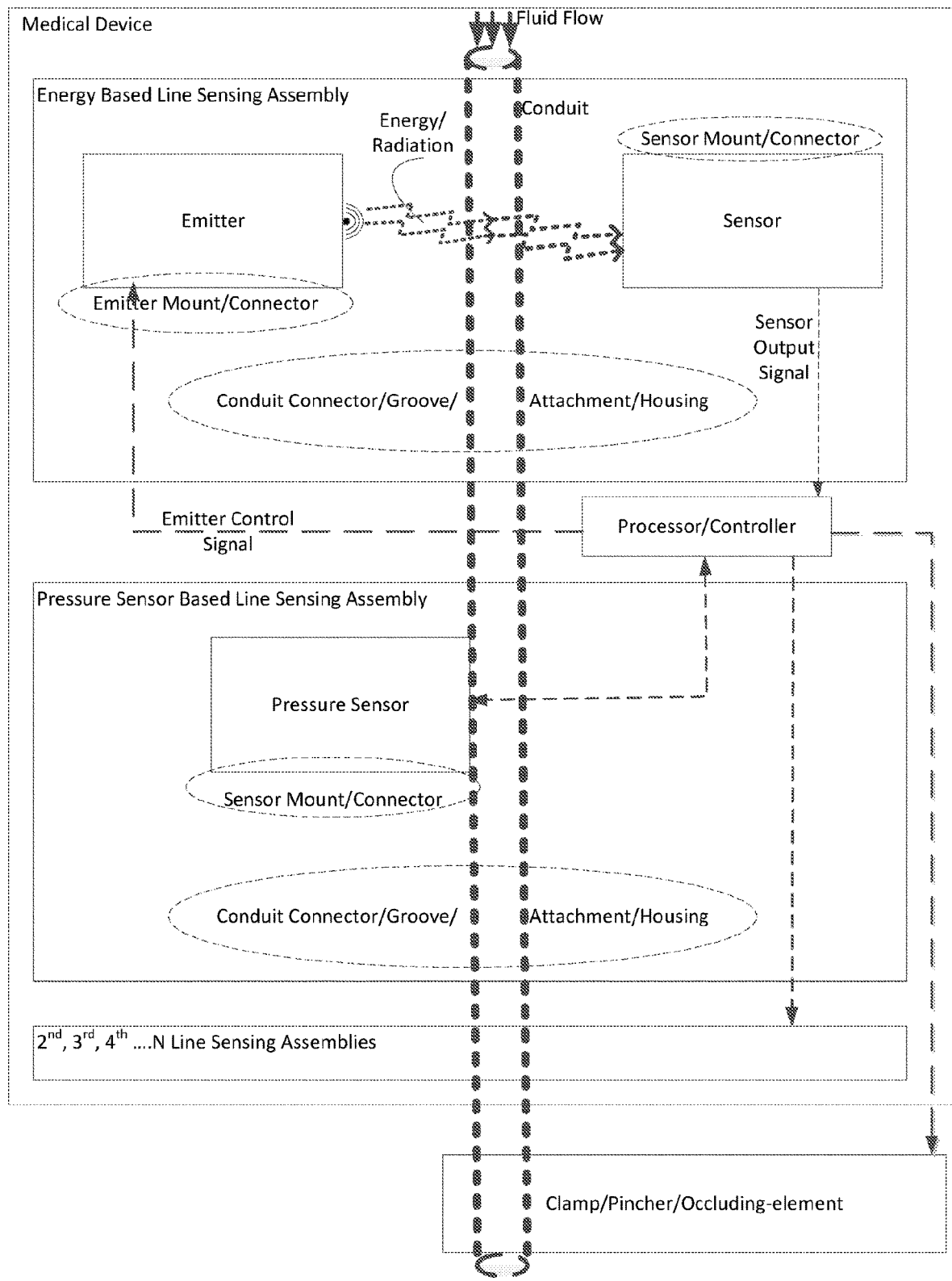
Figure 15B:
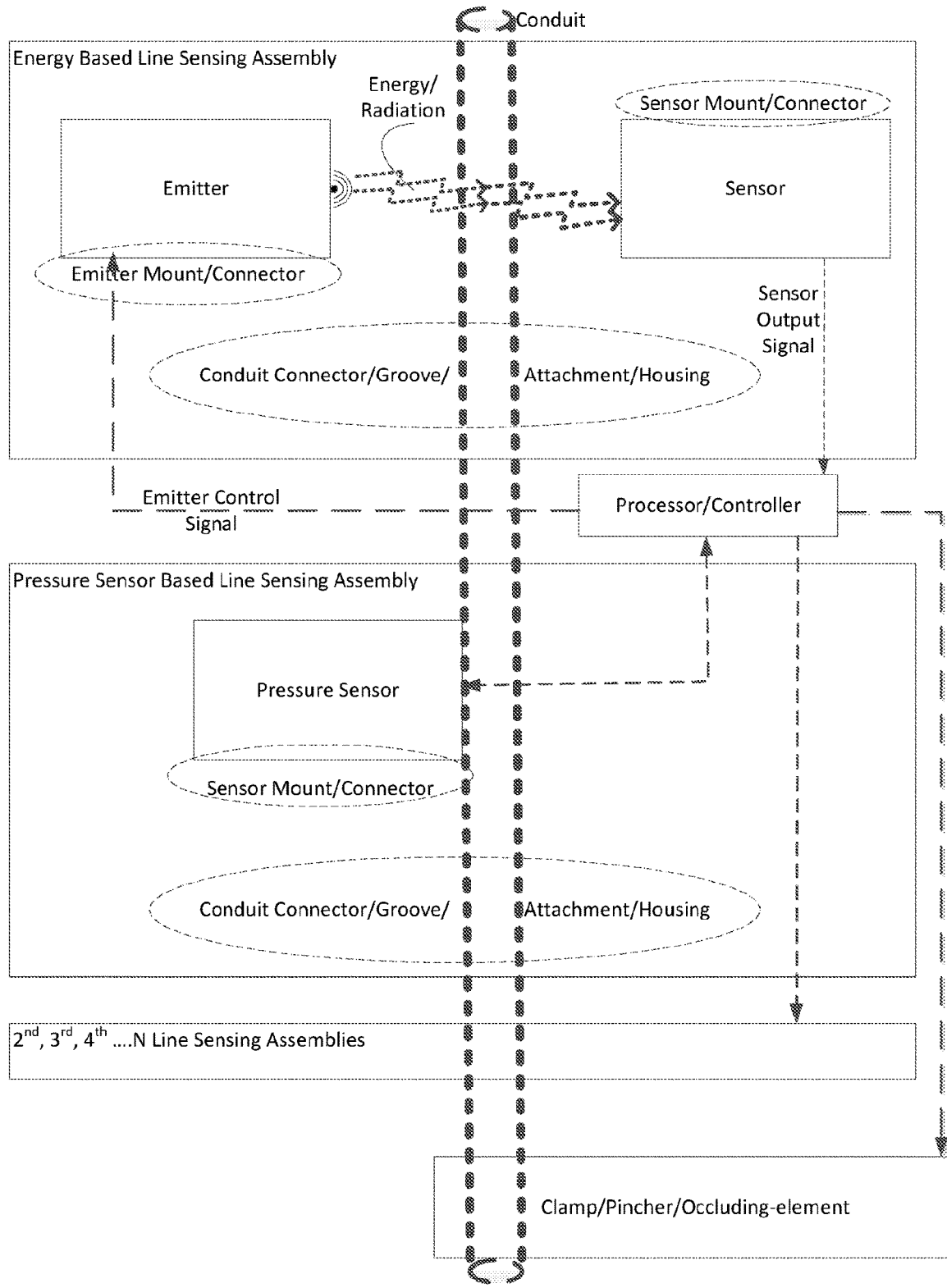

According to some embodiments, as illustrated in FIG. 7, a method of air bubble detection may include: receiving an output from a sensor, analyzing the output to determine if an air bubble is detected; if air is detected, analyzing the output to determine if the air bubble is static or dynamic. If the air bubble is dynamic then further analysis may be carried out to determine if a determined air clinical threshold is reached, in which case an alarm may be emitted and/or an associated medical device may be stopped. The determined air clinical threshold may be a distinct threshold (for example, if a singular air bubble exceeds an air bubble clinical threshold) or a cumulative threshold (if a volume of air over a defined period of time is exceeded), a combination of the two or any other relevant threshold. Static air bubbles may also be monitored, once identified, to detect when they become mobile. An exemplary process for monitoring a conduit including sensing and determining the mobility of detected air bubbles is presented in FIG. 7. According to some embodiments, as shown in FIGS. 14A-15B, the different assemblies for detecting a boundary condition, for carrying out spectral analysis to detect specific fluids, for detecting pressure change in response to a clamp and/or for differentiating between fluid and gas and embodiments relating to detecting of existence of fluid or gas in the line may be used separately or in conjunction with each other and/or may have overlapping functionality. Similarly, as shown in FIGS. 15A-15B, further sensing assemblies may be implemented in conjunction with the sensing assemblies described herein. Further, as shown in FIGS. 14B and 15B, combinations of sensing assemblies may be implemented as integrated components of a medical device, or mounted thereupon, and/or as shown in FIGS. 14A and 15A, combinations of sensing assemblies may be implemented as separate devices designed to function in combination with a fluid delivery system.

U.S. Provisional Patent Application No. 62/185,737, titled: "Medical Device with Improved Air Bubble Detection and Methods for Improved Air Bubble Detection" filed on Jun. 29, 2015; and U.S. Provisional Patent Application No. 62/278,617, titled: "Methods Circuits Devices Assemblies Systems and Associated Computer Executable Code For Detecting a Substance In a Line of a Medical Device" filed on Jan. 14, 2016 are each hereby incorporated by reference into the present Application in their entirety.

It should also be understood by one of skill in the art that some of the functions described as being performed by a specific component of the system may be performed by a different component of the system in other embodiments of this invention.

In the description and claims of embodiments of the present invention, each of the words, "comprise" "include" and "have", and forms thereof, are not necessarily limited to members in a list with which the words may be associated.

Only exemplary embodiments of the present invention and but a few examples of its versatility are shown and described in the present disclosure. It is to be understood that the present invention is capable of use in various other combinations and environments and is capable of changes or modifications within the scope of the inventive concept as expressed herein.

While certain features of the invention have been illustrated and described herein, many modifications, substitutions, changes, and equivalents will now occur to those skilled in the art. It is, therefore, to be understood that the appended claims are intended to cover all such modifications and changes.

The invention claimed is:

1. An assembly for spectral analysis of fluid within a conduit, said assembly comprising:
   a multi-spectral light emitter adapted to emit light in two or more distinct wave bands;
   a multi-spectral light sensor;
   an emitter-line interface and a sensor-line interface, jointly adapted to mount said emitter and said sensor on opposing sides of the conduit; and
   signal processing circuitry communicatively coupled to said sensor and configured to receive and analyze an electrical signal generated by the sensor and, in response to the analyzing, detect parameters indicative of fluid transitions within the conduit to distinguish between liquid and gas for:
      (i) at least a first liquid that has (a) a spectral signature that is similar to air at a first wave band of the two or more distinct wave bands, and (b) a spectral signature that is distinct from air at a second wave band of the two or more distinct wave bands; and
      (ii) at least a second liquid that has (a) a spectral signature that is similar to air at the second wave band, and (b) a spectral signature that is distinct from air at the first wave band.

2. The assembly according to claim 1, wherein said multi-spectral light emitter is a RGB emitter and said two or more distinct wave bands include at least two of the Red, Green and Blue wave bands.

3. The assembly according to claim 1, wherein said signal processing circuitry is further adapted to (i) identify an output of said sensor indicative of an air bubble within the conduit by detecting changes in the parameters indicative of fluid transitions within the conduit and (ii) determine a mobility of the air bubble within the conduit based on a rate of change of one or more of the parameters.

4. The assembly according to claim 1, wherein said signal processing circuitry is further adapted to:
   (i) monitor output of said sensor,
   (ii) identify fluctuations in the monitored output indicative of a transition between fluid types, and
   (iii) identify air bubbles within the conduit based on the identified fluctuations.

5. The assembly according to claim 4, wherein said signal processing circuitry is further adapted to assess a size of an air bubble based on a time lapse between identified signal outputs indicative of transitions between fluid types.

6. The assembly according to claim 5, wherein said signal processing circuitry is further adapted to maintain a cumulative count of air bubbles based on the assessed sizes.

7. The assembly according to claim 1, further comprising:
   a pressure sensor adapted to sense pressure within the conduit;
   a clamp adapted to apply force to the conduit, thereby at least partially obstructing fluid flow through the conduit; and
   a first interface adapted to mount said clamp in position to operate upon the conduit and a second interface adapted to mount said sensor in position to operate upon the conduit, such that the clamp is positioned to at least partially obstruct fluid flow through the conduit and the pressure sensor is positioned to sense pressure within the conduit; and
   wherein said signal processing circuitry is communicatively coupled to said pressure sensor and said clamp and configured to measure a rate of change of pressure within the conduit upon application of said clamp, based on output from said pressure sensor.

8. The assembly according to claim 1, wherein said signal processing circuitry is further adapted to use different wave bands of the two or more wave bands to identify different respective fluids.

9. A medical system for delivery of fluid, said system comprising:
   a pump configured to pump fluid through a conduit;
   a pressure sensor mounted upon the pump and adapted to sense pressure within the conduit;
   a clamp adapted to apply force to the conduit, thereby at least partially obstructing fluid flow through the conduit;
   an interface adapted to attach or secure said clamp to the conduit; such that the clamp is positioned to at least partially obstruct fluid flow through the conduit upon application;
   first signal processing circuitry communicatively coupled to said pressure sensor and said clamp and configured to measure a rate of change of pressure within the conduit upon application of said clamp, based on output from said pressure sensor;
   a multi-spectral light emitter adapted to emit light in two or more distinct wave bands;
   a multi-spectral light sensor;
   an emitter-line interface and a sensor-line interface, jointly configured to mount said emitter and said sensor to said pump, on opposing sides of the conduit; and
   second signal processing circuitry communicatively coupled to said multi-spectral light sensor, and adapted to receive and analyze an electrical signal generated by the multi-spectral light sensor and, in response to the analyzing, detect parameters indicative of fluid transitions within the conduit to distinguish between liquid and gas for:
      (i) at least a first liquid that has (a) a spectral signature that is similar to air at a first wave band of the two or more distinct wave bands, and (b) a spectral signature that is distinct from air at a second wave band of the two or more distinct wave bands; and
      (ii) at least a second liquid that has (a) a spectral signature that is similar to air at the second wave band, and (b) a spectral signature that is distinct from air at the first wave band.

10. The system according to claim 9, wherein said first signal processing circuitry is further adapted to distinguish liquid from gas based on the measured rate of change of pressure within the conduit.

11. The system according to claim 9, further comprising:
    an air-bubble sensing sensor adapted to sense a physical parameter of fluid within the conduit;
    an air-bubble sensing sensor-line interface, adapted to mount said air-bubble sensing sensor in position to sense the physical parameter; and
    air-bubble sensing signal processing circuitry communicatively coupled to said air-bubble sensing sensor and adapted to:
    (i) identify an output of said air-bubble sensing sensor indicative of an air bubble within the conduit, and
    (ii) determine a mobility of the air bubble within the conduit based on a rate of change of the physical parameter.

12. The system according to claim 9, wherein said second signal processing circuitry is adapted to:
(i) monitor output of said multi-spectral light sensor,
(ii) identify fluctuations in the monitored output indicative of a transition between fluid types, and
(iii) identify air bubbles within the conduit based on the identified fluctuations.

13. The system according to claim 12, wherein said second signal processing circuitry is further adapted to assess a size of an air bubble based on a time lapse between identified signal outputs indicative of transitions between fluid types.

14. The system according to claim 13, wherein said second signal processing circuitry is further adapted to maintain a cumulative count of air bubbles based on the assessed sizes.

15. The system according to claim 9, wherein said multi-spectral light emitter is a RGB emitter and said two or more distinct wave bands include at least two of the Red, Green and Blue wave bands.

* * * * *